United States Patent
Morita et al.

(10) Patent No.: US 8,139,819 B2
(45) Date of Patent: Mar. 20, 2012

(54) EYE OPEN/CLOSE RECOGNIZING APPARATUS AND RECORDING MEDIUM

(75) Inventors: Takanori Morita, Kariya (JP); Takashi Hiramaki, Nagoya (JP); Jun Adachi, Obu (JP); Yoshinao Takemae, Yokohama (JP)

(73) Assignee: Aisin Seiki Kabushiki Kaisha, Kariya-shi, Aichi-ken (JP)

( * ) Notice: Subject to any disclaimer, the term of this patent is extended or adjusted under 35 U.S.C. 154(b) by 0 days.

(21) Appl. No.: 13/121,125

(22) PCT Filed: Dec. 2, 2009

(86) PCT No.: PCT/JP2009/070249
§ 371 (c)(1),
(2), (4) Date: Jun. 10, 2011

(87) PCT Pub. No.: WO2010/071021
PCT Pub. Date: Jun. 24, 2010

(65) Prior Publication Data
US 2011/0235919 A1    Sep. 29, 2011

(30) Foreign Application Priority Data
Dec. 17, 2008   (JP) ................................. 2008-320889

(51) Int. Cl.
*G06K 9/00* (2006.01)
(52) U.S. Cl. ........................ 382/103; 382/104; 340/575
(58) Field of Classification Search .................. 382/100, 382/103, 104, 117, 118; 348/77, 78; 340/575, 340/576
See application file for complete search history.

(56) References Cited

U.S. PATENT DOCUMENTS

| | | | | |
|---|---|---|---|---|
| 6,927,694 | B1* | 8/2005 | Smith et al. | 340/576 |
| 7,301,464 | B2* | 11/2007 | Coulter | 340/573.7 |
| 2008/0068186 | A1* | 3/2008 | Bonefas et al. | 340/575 |
| 2008/0212828 | A1* | 9/2008 | Ishida et al. | 382/100 |
| 2008/0238694 | A1 | 10/2008 | Ishida | 340/575 |
| 2010/0202658 | A1* | 8/2010 | Ishida et al. | 382/103 |

FOREIGN PATENT DOCUMENTS

| | | |
|---|---|---|
| JP | 10-143669 A | 5/1998 |
| JP | 2000-198369 A | 7/2000 |
| JP | 3769442 B2 | 4/2006 |
| JP | 2007-257043 A | 10/2007 |
| JP | 2008-212298 A | 9/2008 |
| JP | 2008-257575 A | 10/2008 |

OTHER PUBLICATIONS

International Search Report for International Application No. PCT/JP2009/070249 dated Jan. 12, 2010.

* cited by examiner

*Primary Examiner* — Andrew W Johns
(74) *Attorney, Agent, or Firm* — Sughrue Mion, PLLC

(57) ABSTRACT

A computer (30) obtains a facial image acquired by picking up an image of a person subjected to image pickup from a camera (10), and estimates a facial expression of the person subjected to image pickup based on the obtained facial image. Next, the computer obtains an eye open level of the person subjected to image pickup based on the facial image, and sets a threshold of the eye open level based on the estimated facial expression of the person subjected to image pickup. When the eye open level exceeds the threshold, the computer (30) determines that the eye of the person subjected to image pickup is opened. Moreover, when the eye open level does not exceed the threshold, the computer determines that the eye of the person subjected to image pickup is closed.

10 Claims, 19 Drawing Sheets

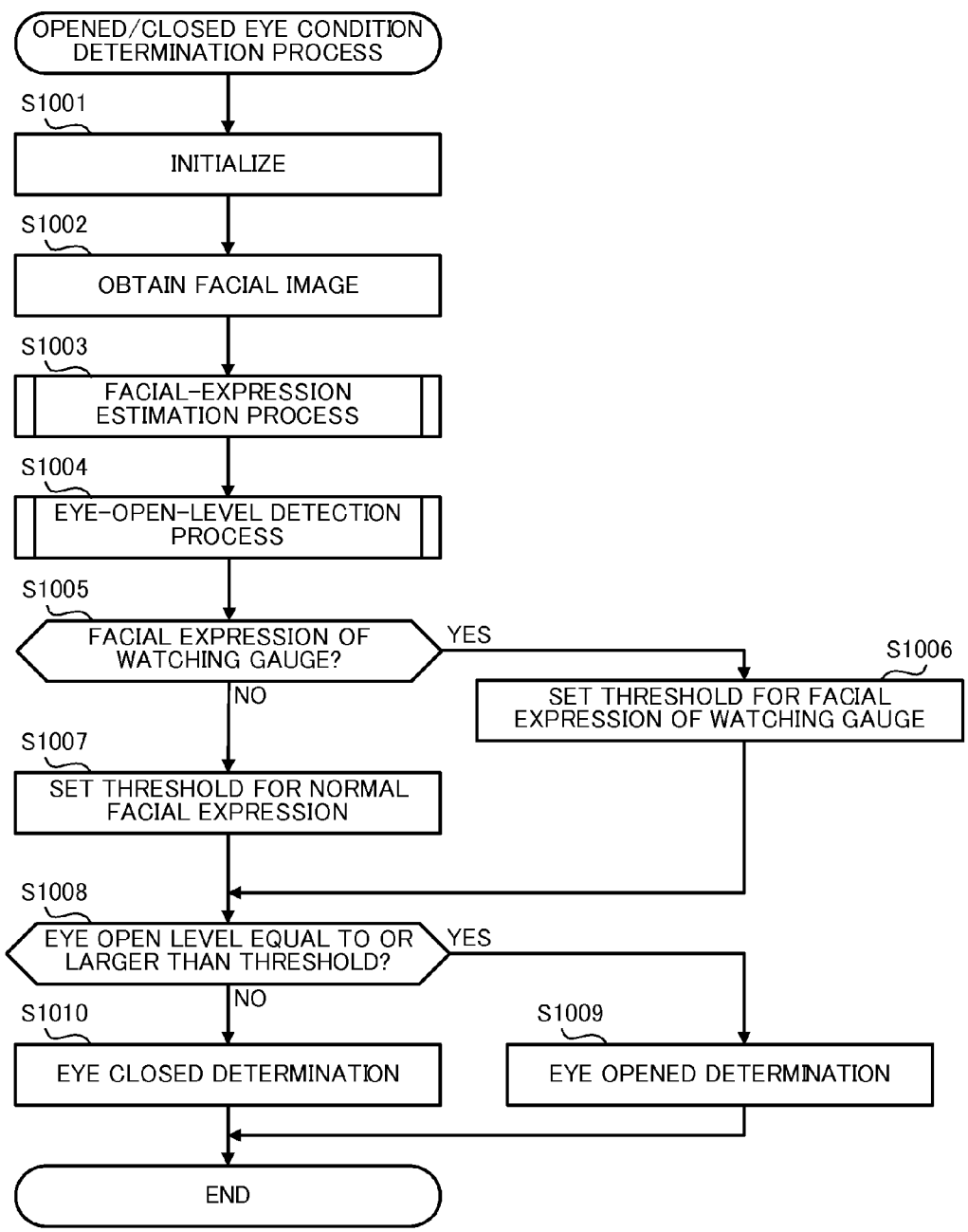

EYE OPEN/CLOSE RECOGNIZING APPARATUS AND RECORDING MEDIUM

CROSS REFERENCE TO RELATED APPLICATIONS

This application is a National Stage of International Application No. PCT/JP2009/070249 filed Dec. 2, 2009, which claims priority from Japanese Patent Application No. 2008-320889 filed Dec. 17, 2008, the contents of all of which are incorporated herein by reference in their entirety.

TECHNICAL FIELD

The present invention relates to an eye open/close recognizing apparatus that is suitable for determining an opened/closed condition of an eye of a person subjected to image pickup based on a facial expression of that person and recording medium storing a program for realizing such an eye open/close recognizing apparatus on a computer.

BACKGROUND ART

Recently, there is known a catnap condition detecting apparatus that determines an opened/closed condition of an eye of a driver based on an image of the face of the driver of a vehicle in order to detect a catnap condition of the driver.

For example, patent literature 1 discloses a catnap condition detecting apparatus that detects a catnap condition of a driver in accordance with a change in a light environment and a difference in the position of the face originating from individual difference of the driver. The catnap condition detecting apparatus disclosed in patent literature 1 detects the open level of an eye from the maximum continuous number of labeled regions included in an eye region in the vertical direction when determining opening/closing of the eye, thereby determining whether or not the eye is opened or closed.

Moreover, patent literature 2 discloses an eye condition detecting apparatus which estimates a situation in which a driver feels brightness, and which corrects an opened/closed eye determination reference, thereby improving the detection precision. The eye condition detecting apparatus disclosed in patent literature 2 learns the maximum value of the open level of the eye and the minimum value thereof from a change in the open level values of the eye in time series output plural times from an eye-open-level detecting circuit, and sets an opened/closed eye determination reference. The eye condition detecting apparatus disclosed in patent literature 2 slightly corrects the opened/closed eye determination reference when determining that the driver feels brightness. Hence, false determination as the eye being closed can be suppressed when the driver has a narrowed eye because of brightness.

Furthermore, patent literature 3 discloses a sleepiness determining apparatus that can determine a sleepiness condition. The sleepiness determining apparatus disclosed in patent literature 3 calculates an open level of an eye based on images of an eye region, obtains a weighting factor relative to the calculated eye open level based on a sigmoidal function, and multiplies the weighting factor by the eye open level, thereby calculating a weighted eye open level. The sleepiness determining apparatus disclosed in patent literature 3 compares the accumulated value of the weighted eye open levels with first and second threshold values both set beforehand, thereby determining a sleepiness level. According to the sleepiness determining apparatus disclosed in patent literature 3, because the eye open level is weighted and accumulated, the sleepiness condition of a driver can be determined in consideration of the contribution of sleepiness with respect to a condition in which the driver opens his/her eyes by half.

Still further, patent literature 4 discloses an eye condition detecting apparatus comprising reference correcting means for learning an opened/closed eye determination reference again when it is detected that a driver just starts driving and the open level of an eye changes. The eye condition detecting apparatus disclosed in patent literature 4 learns the opened/closed eye determination reference again at an appropriate timing in accordance with a situation. For example, when determining that the driver feels brightness because of a change in a light environment, the eye condition detecting apparatus does not learn the opened/closed eye determination reference again. Accordingly, it is possible for the eye condition detecting apparatus to prevent the opened/closed eye determination reference from becoming excessively small, and to avoid determining that the eye is always opened in a condition in which the driver does not feel brightness.

PRIOR ART DOCUMENTS

Patent Literatures

Patent Literature 1: Unexamined Japanese Patent Application KOKAI Publication No. H10-143669
Patent Literature 2: Unexamined Japanese Patent Application KOKAI Publication No. 2000-198369
Patent Literature 3: Unexamined Japanese Patent Application KOKAI Publication No. 2008-212298
Patent Literature 4: Japanese Patent No. 3769442

DISCLOSURE OF INVENTION

Problem to be Solved by the Invention

The apparatuses disclosed in patent literatures 1 to 4, however, do not employ a configuration of determining the opened/closed condition of the eye of a driver appropriately in consideration of the facial expression of the driver, so that such apparatuses may falsely determine the opened/closed condition of the eye of the driver.

For example, the catnap condition detecting apparatus disclosed in patent literature 1 may falsely determine that the eye is closed regardless of the facial expression of the driver because the distance between the eyelids in the vertical direction is close when the driver has a narrowed eye.

The eye condition detecting apparatus disclosed in patent literature 2 estimates the driver's situation based on density information around the eye. Hence, when, for example, the surroundings of the eye are bright, the eye condition detecting apparatus may estimates that the driver feels brightness regardless of the driver's facial expression. Moreover, when the surroundings of the eye are dark, the eye condition detecting apparatus may estimate that the driver does not feel brightness even through the driver feels brightness in reality.

Moreover, the sleepiness determining apparatus disclosed in patent literature 3 is capable of determining the sleepiness level of the driver in consideration of the half-opened condition of the eye, but is unable to determine the sleepiness level appropriately in consideration of the whole facial expression of the driver.

Furthermore, the eye condition detecting apparatus disclosed in patent literature 4 uses the opened/closed eye determination reference generated (relearned) based on past situations as a reference for determination of opening/closing of the eye. Accordingly, the eye condition detecting apparatus disclosed in patent literature 4 is unable to determine whether or not the eye is opened or closed appropriately in accordance with a situation at the time of eye opening/closing determination like the facial expression of the driver at the time of eye opening/closing determination.

The present invention has been made in view of the above-explained problems, and it is an object of the present invention to provide an eye open/close recognizing apparatus that is suitable for determining whether or not the eye of a person subjected to image pickup is opened or closed based on the facial expression of that person and a program for realizing such an eye open/close recognizing apparatus on a computer.

Means for Solving the Problem

In order to accomplish the above object, an eye open/close recognizing(identifying) apparatus of the present invention comprises: image obtaining unit that obtains an image of a face of a person subjected to image pickup; facial-expression estimating unit that estimates a facial expression of the person subjected to image pickup based on the image; eye-open-level obtaining unit that obtains an eye open level of the person subjected to image pickup based on the image; threshold setting unit that sets a threshold to be low when it is determined that facial expression estimated by the facial-expression estimating unit indicates that an awakening level is high, and sets the threshold to be high when it is determined that the facial expression estimated by the facial-expression estimating unit indicates that the awakening level is low; and eye open/close determining unit which determines that an eye of the person subjected to image pickup is opened upon determination that the eye open level exceeds the threshold, and which determines that the eye of the person subjected to image pickup is closed upon determination that the eye open level does not exceed the threshold.

The eye open/close determining unit may determine that the eye of the person subjected to image pickup is opened regardless of the eye open level when it is determined that the facial expression estimated by the facial-expression estimating unit indicates that the awakening level is high, and may determine that the eye of the person subjected to image pickup is closed regardless of the eye open level when it is determined that the facial expression estimated by the facial-expression estimating unit indicates that the awakening level is low.

The threshold setting unit may determine that a smiling facial expression, a squinting facial expression in the glare or a facial expression of watching an object in a specific direction is a facial expression indicating that the awakening level is high.

The threshold setting unit may determine that a sleepy facial expression is a facial expression indicating that the awakening level is low.

The threshold setting unit may determine that a facial expression of watching a gauge of a vehicle driven by the person subjected to image pickup is a facial expression indicating that the awakening level is high.

The eye open/close recognizing apparatus may further comprise record information memory unit that stores, as record information, information indicating the facial expression estimated by the facial-expression estimating unit in association with information indicating an eye open level, in which the threshold setting unit may set the threshold based on the record information.

The record information memory unit may further store, as the record information, the information indicating a facial expression estimated by the facial-expression estimating unit and the information indicating an eye open level in association with information indicating a determination result by the eye open/close determining unit.

The facial-expression estimation unit may estimate a facial expression of the person subjected to image pickup based on the image using a neural network.

The neural network may be a Kohonen type neural network.

The eye-open-level obtaining unit may extract an image including the eye of the person subjected to image pickup from the image, may perform binarization on the extracted image, and may obtain, as the eye open level, the maximum value of the number of pixels which are arranged consecutively in the vertical direction of the eye of the person subjected to image pickup and which have predetermined brightness.

In order to accomplish the above object, a recording medium of the present invention allows a computer to function as: image obtaining unit that obtains an image of a face of a person subjected to image pickup; facial-expression estimating unit that estimates a facial expression of the person subjected to image pickup based on the image; eye-open-level obtaining unit that obtains an eye open level of the person subjected to image pickup based on the image; threshold setting unit that sets a threshold to be low when it is determined that facial expression estimated by the facial-expression estimating unit indicates that an awakening level is high, and sets the threshold to be high when it is determined that the facial expression estimated by the facial-expression estimating unit indicates that the awakening level is low; and eye open/close determining unit which determines that an eye of the person subjected to image pickup is opened upon determination that the eye open level exceeds the threshold, and which determines that the eye of the person subjected to image pickup is closed upon determination that the eye open level does not exceed the threshold.

Effect of the Invention

According to the eye open/close recognizing apparatus and the recording medium of the present invention, it is possible to determine the opened/closed condition of the eye of a person subjected to image pickup based on the facial expression of that person subjected to image pickup.

BRIEF DESCRIPTION OF DRAWINGS

FIG. 19 is a flowchart showing an illustrative opened/closed eye condition determination process executed by an eye open/close recognizing apparatus according to a modified example.

BEST MODE FOR CARRYING OUT THE INVENTION

First Embodiment

An explanation will now be given of an eye open/close recognizing apparatus 100 according to a first embodiment of the present invention with reference to the accompanying drawings.

First, a configuration of the eye open/close recognizing apparatus 100 according to the first embodiment will be explained with reference to FIG. 1.

Figure 1:
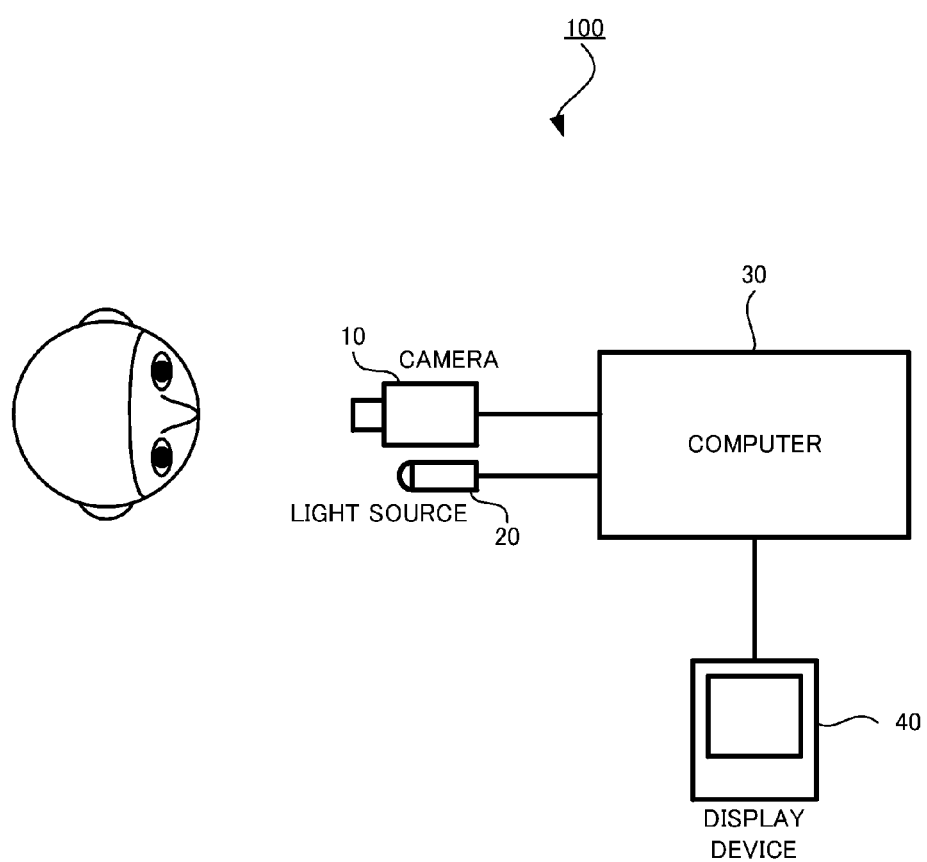
FIG. 1 is a configuration diagram showing an eye open/close recognizing apparatus according to the first to third embodiments of the present invention.

As shown in FIG. 1, the eye open/close recognizing apparatus 100 includes a camera 10 which picks up an image of the face of a driver and which generates an image (a facial image) including the face of the driver, a light source 20 that lights up the face of the driver, a computer 30 that determines the opened/closed condition of the eye of the driver, and a display device 40 that is connected to the computer 30.

The camera 10 obtains images (tone images) each including the face of the driver and the background thereof for each certain cycle (e.g., 1/30 seconds), and successively outputs the obtained images. The camera 10 outputs the obtained images as, for example, analog image signals. To simplify the explanation below, an image which is picked up by the camera 10 and which includes the face of the driver and the background thereof is referred to as a "facial image".

The camera 10 comprises, for example, a CCD (Charge Coupled Device) camera.

The display device 40 displays the facial image picked up by the camera 10 and the like. The display device 40 comprises, for example, an LCD (Liquid Crystal Display) or a CRT (Cathode Ray Tube).

Figure 2:
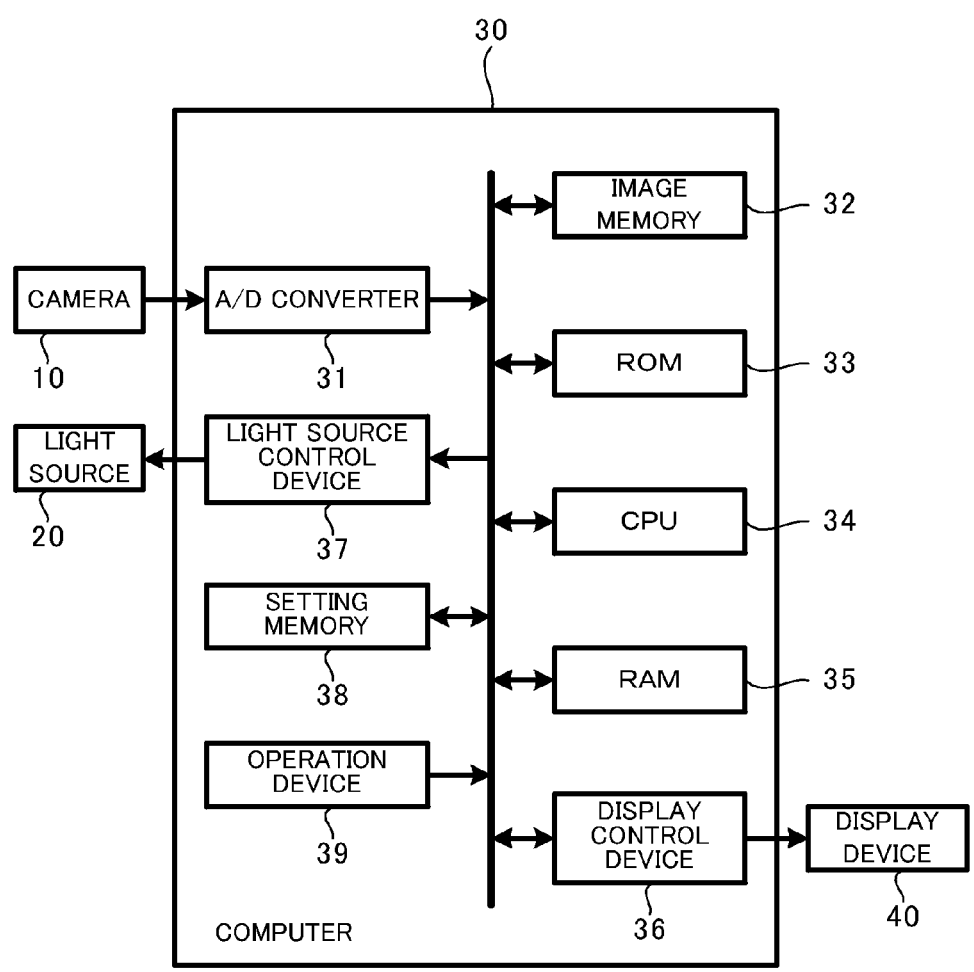
FIG. 2 is a block diagram showing a configuration of a computer shown in FIG. 1.

The computer 30 processes the facial image picked up by the camera 10, and determines the opened/closed condition of the eye of the driver. As shown in FIG. 2, the computer 30 includes an A/D (Analog/Digital) converter 31, an image memory 32, a ROM (Read Only Memory) 33, a CPU (Central Processing Unit) 34, a RAM (Random Access Memory) 35, a display control device 36, a light-source control device 37, a setting memory 38, and an operation device 39.

The A/D converter 31 converts the analog image signal supplied from the camera 10 to a digital image signal, and outputs the converted signal.

The image memory 32 stores a facial image represented by the digital image signal output by the A/D converter 31. The image memory 32 comprises, for example, an SRAM (Static Random Access Memory).

The ROM 33 stores a program that controls the operation of the CPU 34. Moreover, the ROM 33 stores various fixed data for executing image processes to be discussed later.

The CPU 34 controls the whole operation of the computer 30. The CPU 34 runs the program stored in the ROM 33 in order to process the facial image generated by the camera 10, thereby determining the opened/closed condition of the eye of the driver.

The RAM 35 functions as a work area for the CPU 34.

The display control device 36 converts, for example, the facial image stored in the image memory 32 to data in a format displayable by the display device 40 under the control of the CPU 34, and supplies the converted data to the display device 40.

The light-source control device 37 controls turn on/off of the light source 20.

The setting memory 38 stores data (hereinafter, referred to as "setting information") like a facial-expression map and a clustering result to be discussed later which are used when the CPU 34 processes the facial image and determines the opened/closed condition of the eye.

The operation device 39 receives an operation given by a user, and supplies an operation signal in accordance with the operation to the CPU 34.

Next, with reference to the flowchart of FIG. 3, an explanation will be given of an opened/closed eye condition determination process executed by the opened/closed eye recognizing apparatus 100.

Figure 3:
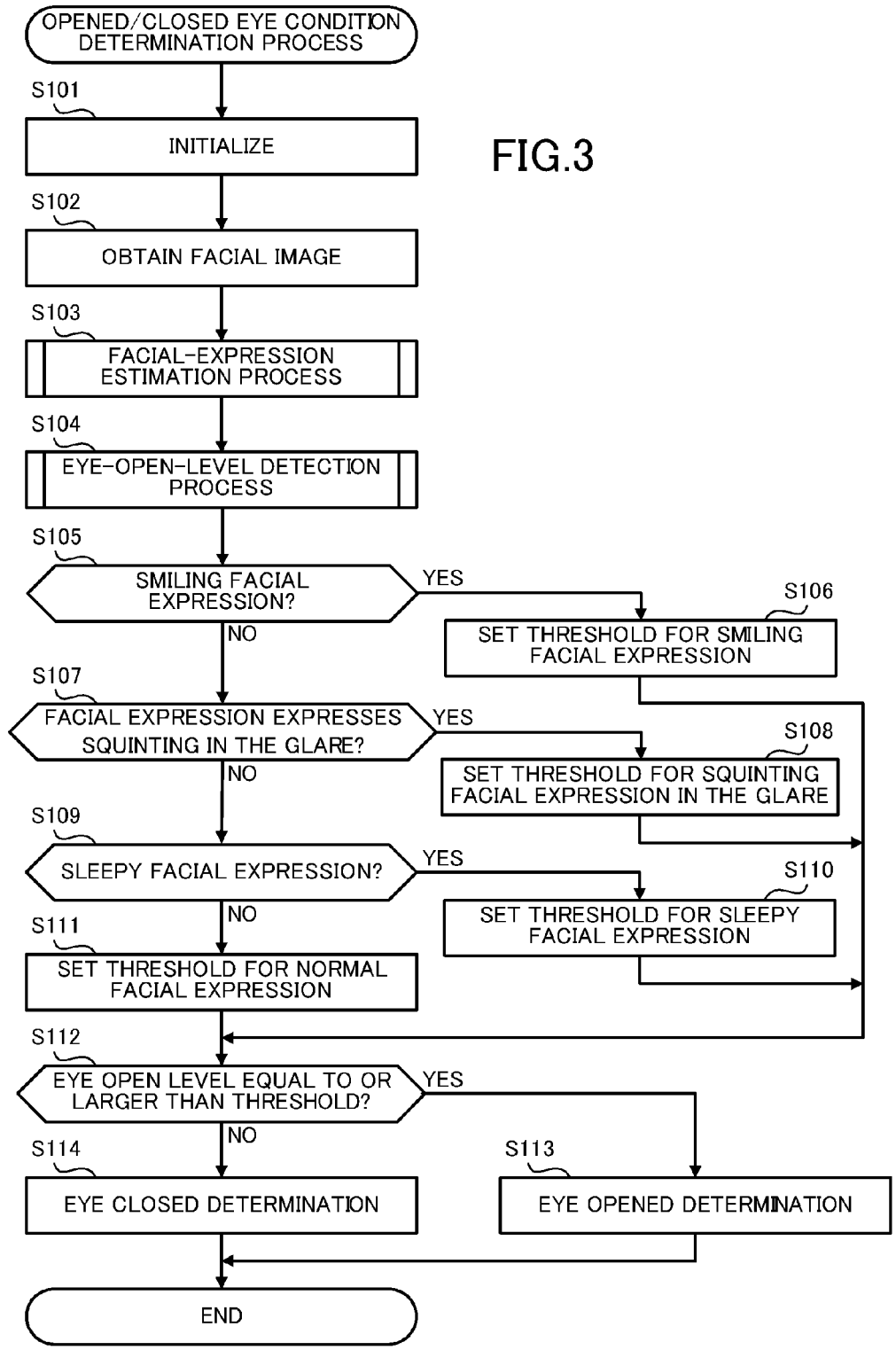
FIG. 3 is a flowchart showing an illustrative opened/closed eye condition determination process executed by the eye open/close recognizing apparatus according to the first embodiment of the present invention.

Upon power on of the eye open/close recognizing apparatus 100, the CPU 34 in the computer 30 periodically (e.g., for each 1/30 seconds) executes the opened/closed eye condition determination process shown in FIG. 3.

First, the CPU 34 executes, for example, initialization of a variable used for the opened/closed eye determination process (step S101).

Next, the CPU 34 obtains the facial image of the driver (step S102). More specifically, the CPU 34 supplies the facial image expressed by analog image signals by what corresponds to a frame output by the camera 10 to the A/D converter 31, and a facial image expressed by digital image signals by what corresponds to a frame output by the A/D converter 31 is stored in the image memory 32.

Next, the CPU 34 executes a facial-expression estimation process (step S103). The facial-expression estimation process executed by the CPU 34 is not limited to any particular process as long as it can estimate a facial expression from the facial image. In the present embodiment, an explanation will be given of a process that estimates a facial expression through a Kohonen neural network.

Figure 4:
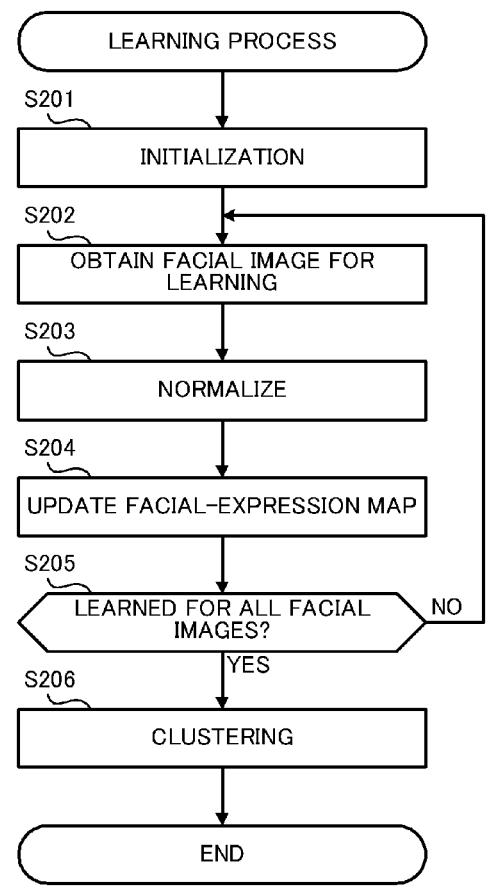
FIG. 4 is a flowchart showing an illustrative learning process executed by the eye open/close recognizing apparatus according to the first embodiment of the present invention.

When a facial expression is estimated through the Kohonen neural network, it is necessary to learn a rule beforehand regarding what facial expression is estimated from what a facial image is input. An explanation will now be given of a learning process executed by the CPU 34 prior to execution of the facial-expression estimation process (step S103) with reference to FIG. 4.

The CPU 34 initializes a variable, etc., used for the learning process (step S201). Moreover, the CPU 34 initializes the facial-expression map to be discussed later, i.e., gives a small value to a network joint weight of each unit in order to perform initialization.

Next, the CPU 34 obtains a facial image for learning (step S202). For example, the CPU 34 supplies a facial image expressed by analog image signals by what corresponds to a frame output by the camera 10 picked up the image of the driver with each facial expression to the A/D converter 31, and obtains a facial image expressed by digital image signals by what corresponds to a frame output by the A/D converter 31 as a facial image for learning.

An explanation will now be given of a facial image for learning with reference to the accompanying drawings.

Figure 5A:
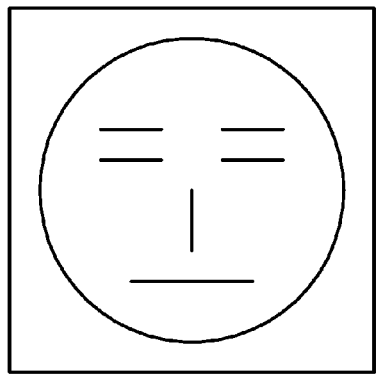
FIG. 5A is a diagram showing a (first) facial image for learning.
Figure 5B:
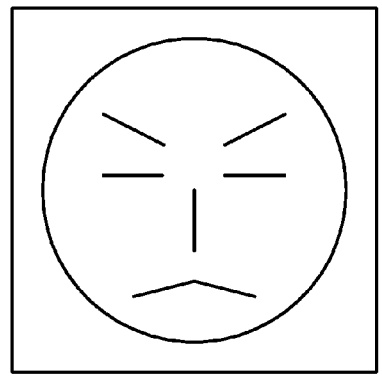
FIG. 5B is a diagram showing a (second) facial image for learning.
Figure 5C:
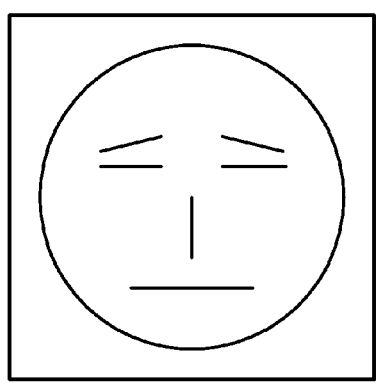
FIG. 5C is a diagram showing a (third) facial image for learning.
Figure 5D:
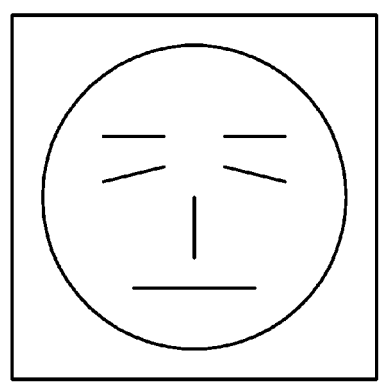
FIG. 5D is a diagram showing a (fourth) facial image for learning.
Figure 5E:
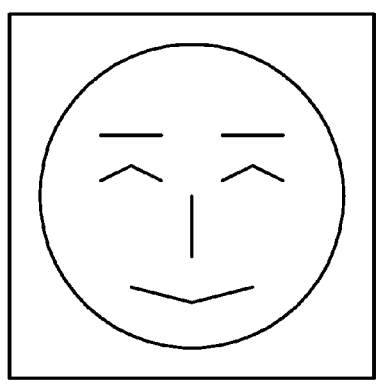
FIG. 5E is a diagram showing a (fifth) facial image for learning.
Figure 5F:
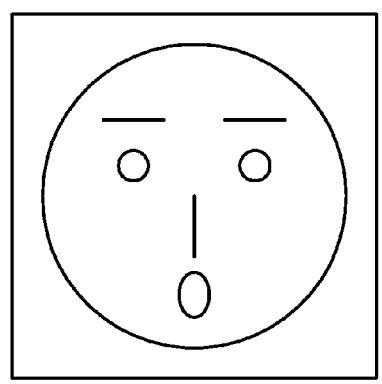
FIG. 5F is a diagram showing a (sixth) facial image for learning.

FIGS. 5A to 5F show illustrative facial images for learning. FIG. 5A is an illustrative facial image obtained when the image of the driver with "no expression" is picked up. FIG. 5B is an illustrative facial image obtained when the image of the driver with "anger" is picked up. FIG. 5C is an illustrative facial image obtained when the image of the driver feeling "squinting in the glare" is picked up. FIG. 5D is an illustrative facial image obtained when the image of the driver who is "sleepy" is picked up. FIG. 5E is an illustrative facial image obtained when the image of the driver who is "smiling" is picked up. FIG. 5F is an illustrative facial image obtained when the image of the driver who is "surprised" is picked up.

The CPU 34 obtains the facial images of individual facial expressions exemplified in FIGS. 5A to 5F. The facial expressions are not limited to the six kinds explained above, but in order to simplify the explanation, it is presumed that the facial expressions are classified into any one of the above-explained six kinds.

The CPU 34 normalizes the obtained facial image for learning to a facial image in a predetermined format (step S203). For example, the CPU 34 performs gray scaling on the obtained facial image for learning, and corrects the direction of the face and the size of the face based on the positions of both eyes through affine transformation. Next, the CPU 34 cuts out an image around the position of the nose at a predetermined size (e.g., 256 by 256 pixels), and compresses the cut-out image into a predetermined size (e.g., 64 by 64 pixels). The CPU 34 stores the compressed facial image in the image memory 32.

Next, the CPU 34 updates the facial-expression map (step S204). More specifically, the CPU 34 executes various calculations using following formulae (1) to (4), thereby updating the facial-expression map. The facial-expression map includes the obtained facial images for learning (hereinafter, referred to as "input images") each having a size of 64 pixels (a k direction) by 64 pixels (an l direction), and images (hereinafter, referred to as "units") having the same size as those of the input images are arranged i number by j number in the k direction and the l direction, respectively.

It is presumed that the brightness of each pixel of the input image is $x_{kl}$, and the brightness (hereinafter, referred to as a "network joint weight") of each pixel of a unit with coordinates of (i, j) is $w_{ijkl}$, then, a similarity $u_{ij}$ of a unit with coordinates of (i, j) to the input image can be obtained from the formula (1). The CPU 34 specifies a unit having the maximum similarity $u_{ij}$ as a similarity-maximum unit.

[Equation 1]

$$u_{ij} = \frac{\sum x_{kl} w_{ijkl}}{\sqrt{\sum x_{kl}^2 \sum w_{ijkl}^2}} \quad (1)$$

Next, the CPU 34 corrects the joint weight within a vicinity radius d around the similarity-maximum unit so that the joint weight becomes close to $x_{kl}$ using the formulae (2) to (4). Note that $w'_{ijkl}$ is a network joint weight after updating, $w_{ijkl}$ is a network joint weight before updating, $d_s$ is a vicinity radius, $d_i$ and $d_j$ are distances in the i direction and the j direction from a most-appropriate coherent unit to a weight to be updated, T is the total number of learning, t is a current number of learning, and $\alpha(t)$ is a learning coefficient.

[Equation 2]

$$w'_{ijkl} = w_{ijkl} + f(d_i)f(d_j)\alpha(t)(x_{kl} - w_{ijkl}) \quad (2)$$

[Equation 3]

$$f(X) = \cos\left(\frac{\pi X}{2d_s}\right) \quad (3)$$

[Equation 4]

$$\alpha(t+1) = \alpha(t)\left(1 - \frac{t}{T}\right) \quad (4)$$

Like the formula (3), by setting f(X), a gradual change is caused in the facial expression. Moreover, by setting the learning coefficient like the formula (3), the learning coefficient becomes small as the learning advances. That is, the update amount of weight decreases as the distance from the similarity-maximum unit over the map becomes large, and also decreases as the learning advances.

Next, the CPU 34 determines whether or not learning completes for all facial images for learning (step S205). The CPU 34 determines whether or not the current number of learning matches the total number of learning, and when determining that the current number of learning matches the total number of learning (step S205: YES), the process progresses to clustering (step S206), and when the current number of learning does not match (step S205: NO), the process returns to the step of obtaining a facial image (step S202). That is, until determining that the current number of learning matches the total number of learning, the CPU 34 repeats the process from the step of obtaining a facial image (step S202) to the step of updating the facial-expression map (step S204), thereby repeating updating of the facial-expression map.

When determining that the current number of learning matches the total number of learning (step S205: YES), the CPU 34 executes clustering (step S206). That is, the CPU 34 regionalizes the facial-expression map after leaning for each facial expression.

Figure 6:
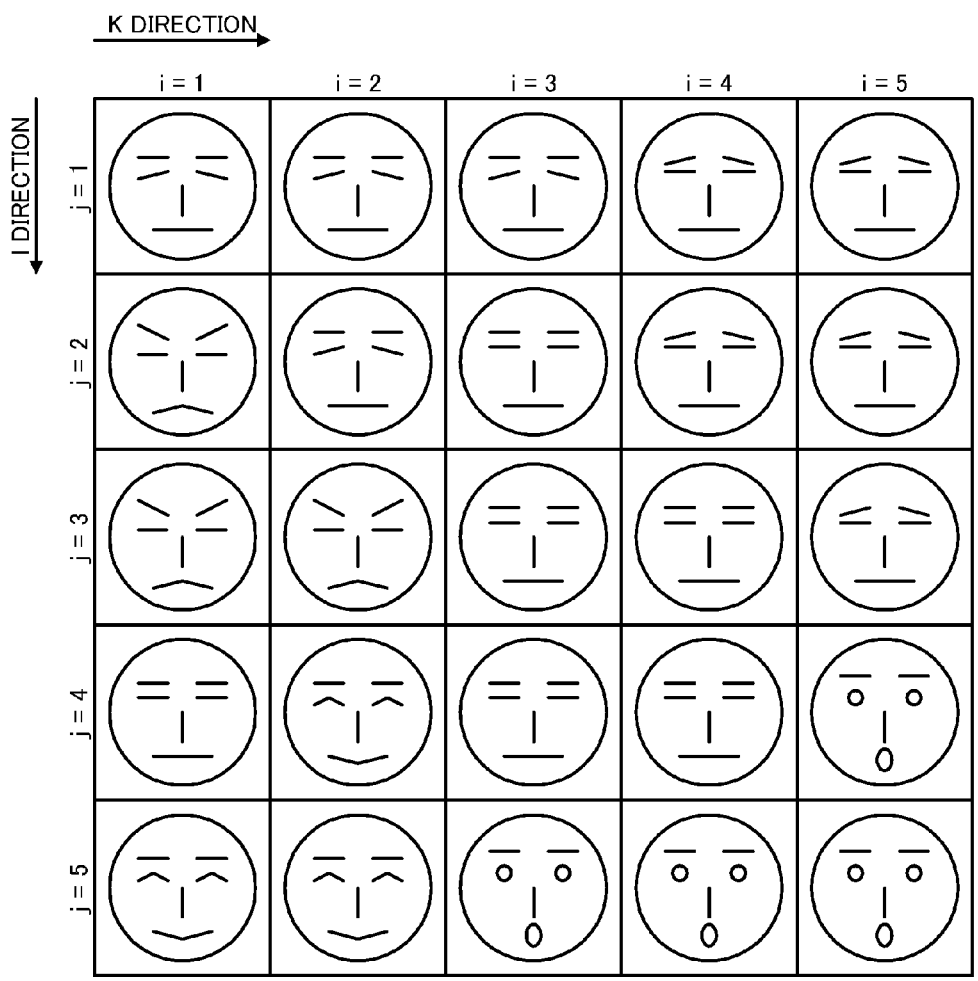
FIG. 6 is a diagram for explaining a facial-expression map after learning.

FIG. 6 exemplifies a facial-expression map updated by what corresponds to the total number of learning through the process from the step of obtaining the facial image for learning (step S202) to the step of updating the facial-expression map (step S204). As shown in FIG. 6, each unit of the facial-expression map after learning is formed with an image representing a facial expression. Note that each unit of the facial-expression map before learning, i.e., the facial-expression map right after initialization (step S201) by the CPU 34 is formed with no image representing a facial expression. This is because a random value is just allocated to each unit as a network joint weight.

Figure 7A:
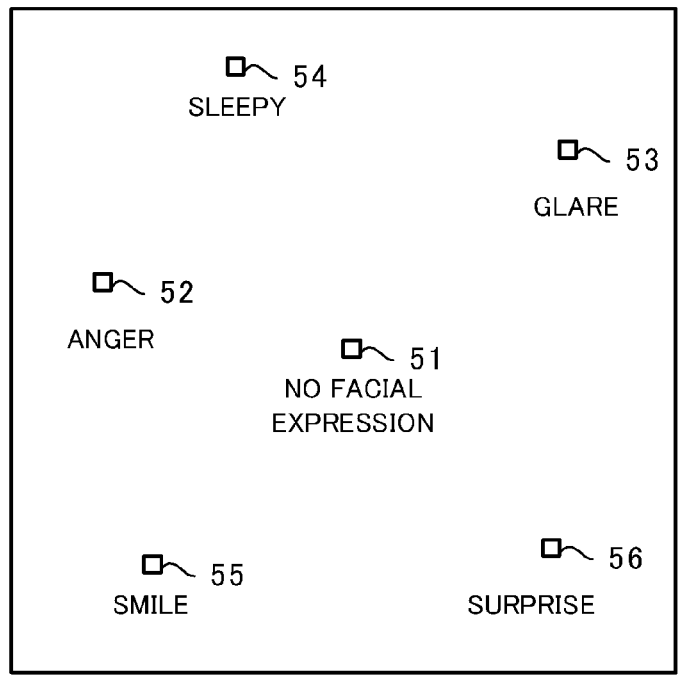
FIG. 7A is a diagram for explaining a (first) regionalization of the facial-expression map.

The CPU 34 obtains the similarity-maximum position of each facial expression based on the facial-expression map shown in FIG. 6. The CPU 34 obtains a similarity-maximum position 51 of the facial image with "no expression" shown in FIG. 7A, a similarity-maximum position 52 of the facial image with "anger", a similarity-maximum position 53 of the facial image in "squinting in the glare", a similarity-maximum position 54 of the facial image with a "sleepiness", a similarity-maximum position 55 of the facial image with a "smile", and a similarity-maximum position 55 of the facial image with a "surprise". For example, the CPU 34 obtains the similarity-maximum position of the facial image of each facial expression from the user through the operation device 39.

Figure 7B:
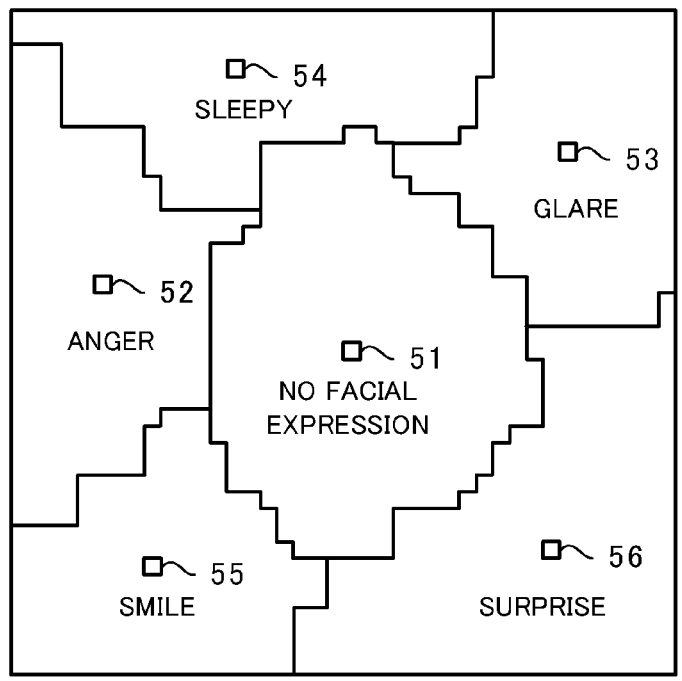
FIG. 7B is a diagram for explaining a (second) regionalization of the facial-expression map.

Next, the CPU 34 performs clustering with the similarity-maximum position of a facial expression f being as a centroid vector $X_f$, and regionalizes the facial-expression map as shown in FIG. 7B. Regionalization is performed through clustering with the facial expression f having a minimum $d_f$ obtained from a formula (5) relative to a neuron $w_{ij}$ at coordinates (i, j) on the facial-expression map being as an expression of that neuron $w_{ij}$. The CPU 34 stores the facial-expression map and a clustering result as setting information in the setting memory 38.

[Equation 5]

$$d_f = |w_{ij} - X_f| \qquad (5)$$

When completing clustering (step S206), the CPU 34 stores the facial-expression map and the clustering result as setting information in the setting memory 38, and completes the learning process.

The CPU 34 executes the learning process explained above before executing the facial-expression estimation process (step S103).

Figure 8:
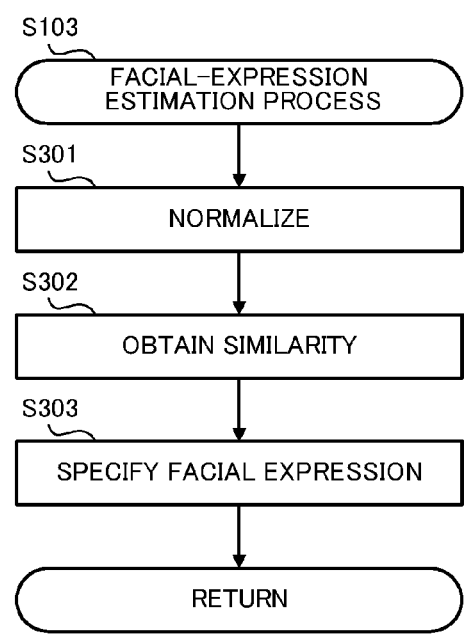
FIG. 8 is a flowchart showing a detail of an illustrative facial-expression estimation process shown in the flowchart of FIG. 3.

Next, an explanation will be given of the facial-expression estimation process (step S103) executed by the eye open/close recognizing apparatus 100 with reference to the flowchart of FIG. 8. The explanation will be given of a case in which the eye open/close recognizing apparatus 100 estimates a facial expression through a similarity-maximum position technique.

The CPU 34 normalizes the facial image stored in the image memory 32 to a facial image with a predetermined format (step S301). For example, the CPU 34 performs gray scaling on the facial image stored in the image memory, and corrects the direction of the face and the size of the face based on the positions of both eyes through affine transformation.

Next, the CPU 34 cuts out an image around the position of the nose at a predetermined size (e.g., 256 by 256 pixels), and compresses the cut image to a predetermined size (e.g., 64 by 64 pixels). The CPU 34 stores the compressed image in the image memory 32.

Next, the CPU 34 obtains a similarity (step S302). With the compressed facial image stored in the image memory 32 being as an input image, the CPU 34 obtains a similarity between the input image and each unit configuring the facial-expression map stored in the setting memory 38 through the formula (1).

Thereafter, the CPU 34 specifies a facial expression (step S303). The CPU 34 obtains a unit having the maximum similarity obtained in the step S302, and specifies the facial expression of the region where that unit belongs as the facial expression of the driver. The CPU 34 stores information (hereinafter, referred to as "estimated facial-expression data") indicating the specified facial expression in the RAM 35.

Upon completion of specifying of the facial expression (step S303), the CPU 34 completes the facial-expression estimation process (step S103).

Figure 9:
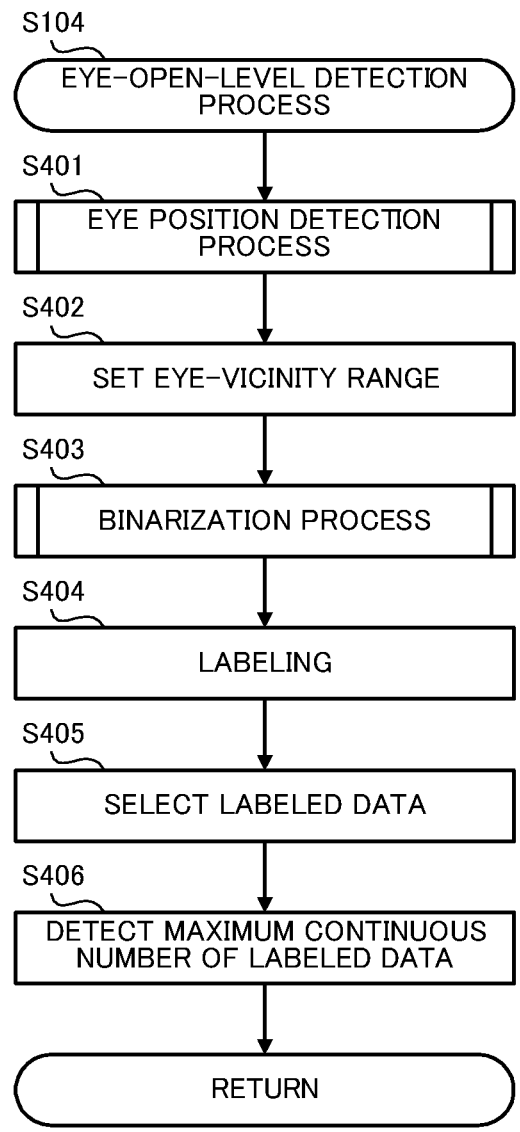
FIG. 9 is a flowchart showing a detail of an illustrative eye-open-level detection process shown in the flowchart of FIG. 3.

When completing the facial-expression estimation process (step S103), the CPU 34 executes an eye-open-level detection process (step S104). An explanation will now be given of the eye-open-level detection process in detail with reference to the flowchart of FIG. 9. It is a rare case in which the driver driving a vehicle opens only one eye and closes another eye. Accordingly, in order to simplify the explanation below, an explanation will be given of a case in which an open level is detected only for either one of the eyes through the eye-open-level detection process.

Figure 10:
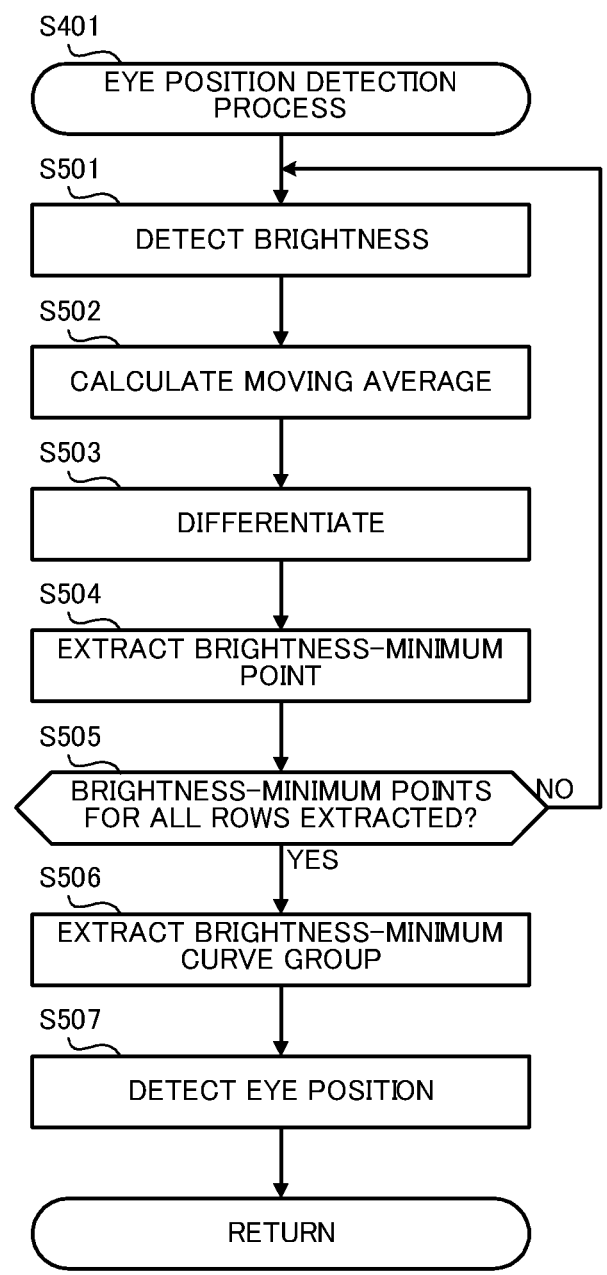
FIG. 10 is a flowchart showing a detail of an illustrative eye position detection process shown in the flowchart of FIG. 9.
Figure 11A:
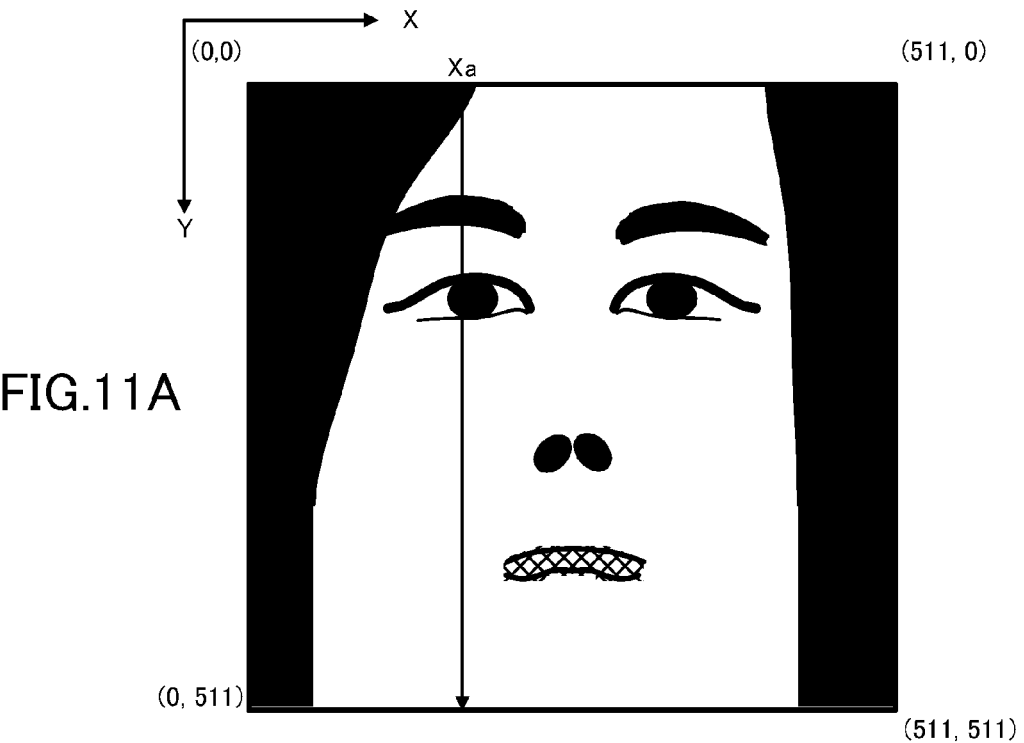
FIG. 11A is a diagram showing an illustrative facial image.

First, the CPU 34 executes an eye-position detection process (step S401). The eye-position detection process will be explained in detail with reference to the flowchart of FIG. 10. FIG. 11A shows an illustrative facial image obtained in the step of obtaining the facial image (step S102). It is presumed that this facial image is in a bitmap format with 24 bits for a pixel and has a size of 512 pixels (x-axis direction) by 512 pixels (y-axis direction).

The CPU 34 detects the brightness of each pixel configuring a selected row (step S501). In the case of the example shown in FIG. 11A, the selected row has an X coordinate which is Xa. The CPU 34 obtains respective brightness for all 512 pixels in the selected row. The CPU 34 obtains, for example, the average value of the tone values (0 to 255) of respective pixels in each color (R, G, and B), and sets the obtained average value as the brightness of the pixel.

Figure 11B:
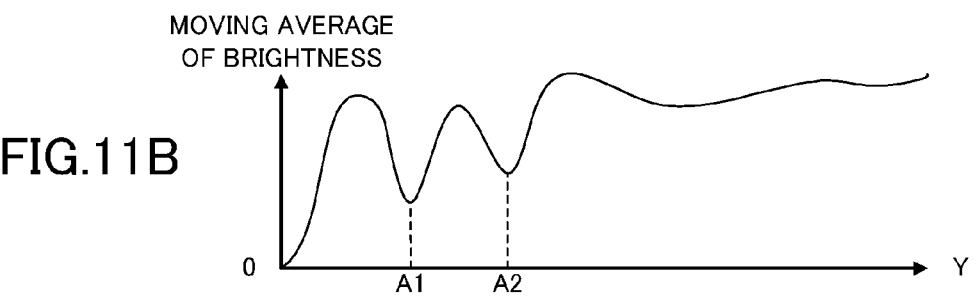
FIG. 11B is a diagram for explaining a (first) method of extracting a brightness minimal point.

Next, the CPU 34 obtains a moving average of the brightness of each pixel configuring the selected row (step S502). The CPU 34 calculates a moving average of the brightness of, for example, 10 pixels successive in the Y-axis direction in an order of a smaller Y coordinate. FIG. 11B shows a relationship between the moving average of brightness and a Y coordinate in a row having an X coordinate which is Xa.

The reason why the moving average of brightness is obtained in the step S502 is to reduce an effect of a local change in brightness and to get a comprehensive change in brightness in a process to be discussed later.

Figure 11C:
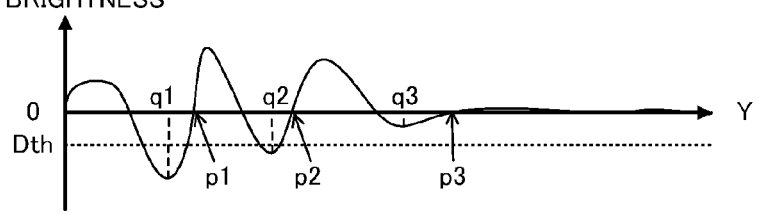
FIG. 11C is a diagram for explaining a (second) method of extracting a brightness minimal point.

Next, the CPU 34 differentiates the moving average of brightness obtained in the step S502 with a variable indicating a position in the Y-axis direction (step S503). FIG. 11C shows a relationship between a differentiated value of the moving average of brightness and a Y coordinate in a row having an X coordinate which is Xa.

Next, the CPU 34 extracts a coordinate where the brightness becomes minimum (hereinafter, referred to as a "brightness-minimum point") (step S504). In the case of the example shown in FIG. 11C, first, the CPU 34 extracts brightness-minimum points p1 to p3 where the differentiated value changes from negative to positive. Next, for each of the detected brightness-minimum points p1 to p3, the CPU 34 determines whether or not brightness of such a point changes largely on some level. More specifically, for each of the brightness-minimum points p1 to p3, the CPU 34 extracts points q1 to q3 right before the differentiated value becomes minimum, and determines whether or not each of the points q1 to q3 is equal to or smaller than a predetermined threshold Dth.

In the case of the example shown in FIG. 11C, the points equal to or smaller than the threshold Dth are the point q1 and the point q2, and the point q3 is not equal to or smaller than the threshold Dth. Accordingly, the CPU 34 excludes the brightness-minimum point p3 from the brightness-minimum points p1 to p3, and extracts the brightness-minimum point p1 and the brightness-minimum point p2 as a brightness-minimum point A1 and a brightness-minimum point A2, respectively.

Next, the CPU 34 determines whether or not extraction of brightness-minimum points for all rows completes, i.e., whether or not the process from detection of the brightness (step S501) to extraction of the brightness-minimum point (step S504) for all rows completes (step S505). When determining that extraction of the brightness-minimum point for all rows completes (step S505: YES), the CPU 34 extracts a brightness-minimum curve group (step S506). When determining that extraction of the brightness-minimum point for all rows does not complete yet (step S505: NO), the CPU 34 executes the process from detection of brightness (step S501) to extraction of a brightness-minimum point (step S504) on a row where extraction of a brightness-minimum point does not complete yet.

Figure 12:
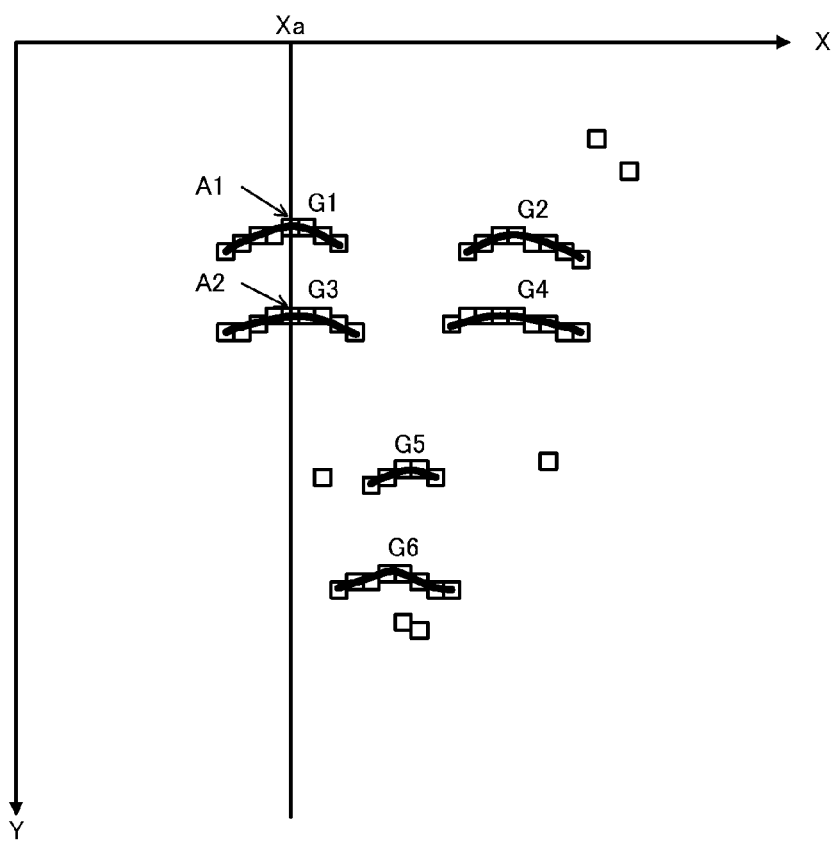
FIG. 12 is a diagram for explaining a method of extracting brightness minimal curve groups.

When determining that extraction of a brightness-minimum point for all rows completes (step S505: YES), the CPU 34 extracts a brightness-minimum curve group (step S506). The CPU 34 sequentially plots the extracted brightness-minimum points for each row, and plots the extracted brightness-minimum points for all rows. FIG. 12 shows an illustrative distribution of all of the extracted brightness-minimum points. For example, when the CPU 34 extracts the brightness-minimum point A1 and the brightness-minimum point A2 in the Xa row, the CPU 34 plots those brightness-minimum points A1 and A2, and plots brightness-minimum points likewise extracted in other rows. As shown in FIG. 12, there are brightness-minimum curves G1 to G6 configured by successive brightness-minimum points around both eyebrows, both eyes, a nose, and a mouth. The CPU 34 detects the brightness-minimum curve group.

How to detect the brightness-minimum curve is optional, but when, for example, points having a difference in the X coordinate which is one, and having a difference in the Y coordinate which is within five are connected together, a brightness-minimum point group having the number of brightness-minimum points connected together which is equal to or larger than three is detected, and the detected brightness-minimum point group can be taken as a brightness-minimum curve. FIG. 12 shows an example case in which six brightness-minimum curves G1 to G6 are detected. As an attribute of the brightness-minimum curve, in addition to the coordinates of each point configuring the brightness-minimum curve, the CPU 34 stores a curve number that is a serial number of the brightness-minimum curve, a curve length that is the number of brightness-minimum points configuring the brightness-minimum curve, a center X coordinate that is an average value of X coordinates of all brightness-minimum points configuring the brightness-minimum curve, and a center Y coordinate that is an average value of Y coordinates of all brightness-minimum points configuring the brightness-minimum curve in the RAM 35.

Next, the CPU 34 detects the positions of the eyes based on the attribute of each brightness-minimum curve (step S507). How to detect the position of the eye is optional, but for example, based on a general characteristic of the eye, a brightness-minimum curve representing the characteristic of the eye well is extracted from the brightness-minimum curves obtained in the step S506, and the position of the eye is obtained from the attribute of that brightness-minimum curve.

For example, conditions are set such that "an eye is long in the horizontal direction", "an eye is in an arcuate shape protruding upwardly", "the position of an eye in the horizontal direction is apart from the center of the face", and "an eye is present below an eyebrow". When such conditions are set, the CPU 34 extracts, for example, a brightness-minimum curve with a curve length of equal to or longer than five based on a condition that "an eye is long in the horizontal direction". Next, the CPU 34 extracts, based on a condition that "an eye is in an arcuate shape protruding upwardly", a brightness-minimum curve having both Y coordinate of a brightness-minimum point with the smallest X coordinate among the brightness-minimum points configuring the brightness-minimum curve and Y coordinate of a brightness-minimum point with the largest X coordinate among the brightness-minimum points configuring the brightness-minimum curve larger than the center Y coordinate.

The CPU 34 extracts, based on a condition that "the position of an eye in the horizontal direction is apart from the center of the face", a curve having a difference which is between the X coordinate of the weighted center of all brightness-minimum points obtained in the step S504 and the center X coordinate and which is equal to or larger than 10. Moreover, based on a condition that "an eye is present below an eyebrow", when there are two brightness-minimum curves both having a difference which is from the center X coordinate which is less than five, the CPU 34 extracts a brightness-minimum curve having a larger center Y coordinate.

Through the foregoing operation, the CPU 34 extracts a brightness-minimum curve corresponding to an eye from the brightness-minimum curve group, and detects the position of an eye. For example, in the case of the example shown in FIG. 12, the CPU 34 extracts the brightness-minimum curve G3 as a brightness-minimum curve representing a right eye, and extracts the brightness-minimum curve G4 as a brightness-minimum curve representing a left eye. Next, the CPU 34 sets, as the center position of the right eye, coordinates including the center X coordinate of the brightness-minimum curve G3 and the center Y coordinate thereof, and sets, as the center position of the left eye, coordinates including the center X coordinate of the brightness-minimum curve G4 and the center Y coordinate thereof. When completing detection of the positions of the eyes (step S507), the CPU 34 completes the eye-position detection process.

When completing the eye-position detection process (step S401), the CPU 34 sets a predetermined range including the eye (hereinafter, referred to as an "eye-vicinity range") (step S402). The CPU 34 sets the eye-vicinity range based on, for example, the attribute of the brightness-minimum curve extracted as the brightness-minimum curve corresponding to the eye through the eye-position detection process (step S401). More specifically, the CPU 34 sets a range which has, for example, an X coordinate that is within 50 from the center X coordinate of the brightness-minimum curve and which has a Y coordinate that is within 20 from the center Y coordinate of the brightness-minimum curve as the eye-vicinity range.

Figure 13:
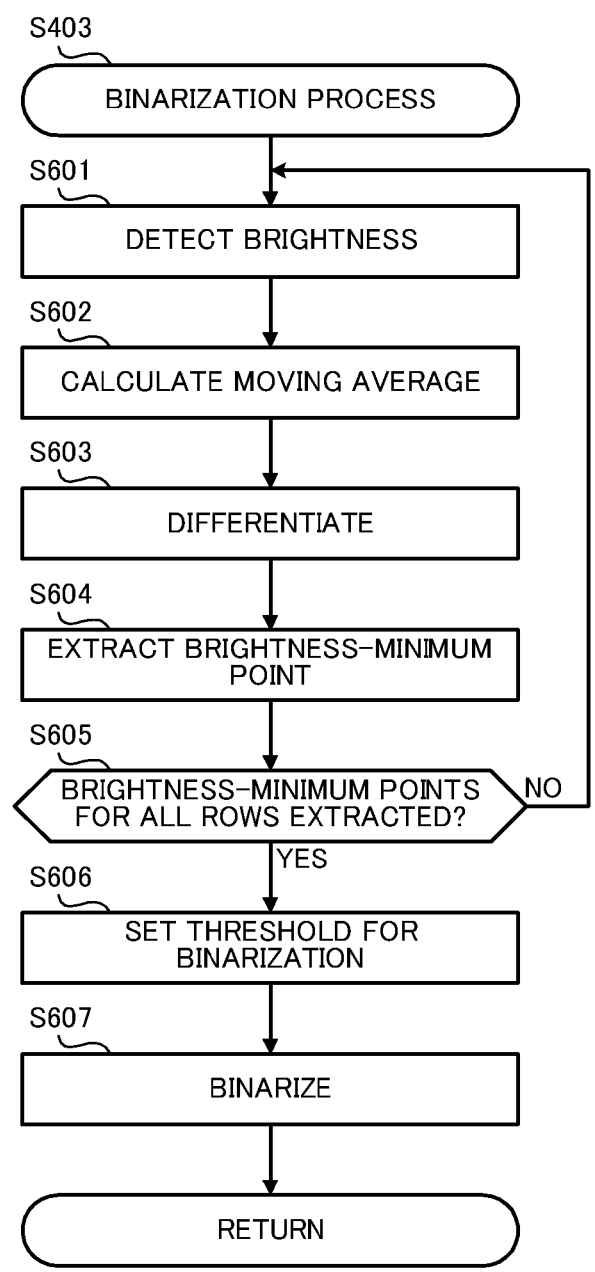
FIG. 13 is a flowchart showing a detail of an illustrative binarization process shown in the flowchart of FIG. 9.

Next, the CPU 34 executes a binarization process (step S403). The binarization process will be explained with reference to the flowchart of FIG. 13.

Figure 14A:
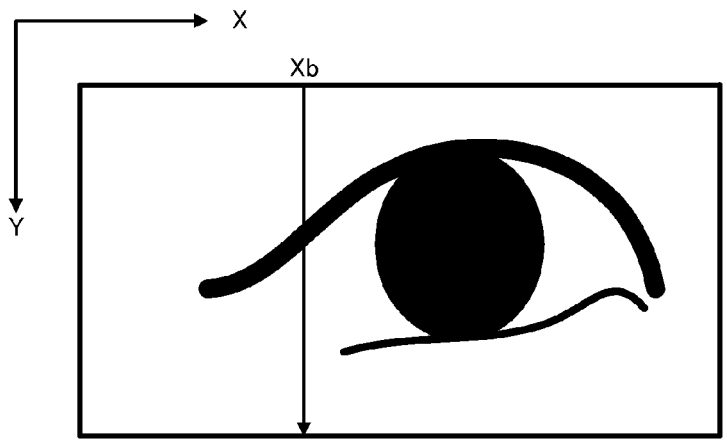
FIG. 14A is a diagram showing an image of eye-vicinity range.

In the binarization process, first, the CPU 34 detects the brightness of each pixel configuring the selected row (step S601). The CPU 34 obtains an average value of the tone values of individual pixels in each color for all pixels of the selected row, and sets the obtained average as the brightness of the pixel. FIG. 14A shows an illustrative image of the eye-vicinity range. The CPU 34 executes the process from the step of detecting brightness (step S601) to the step of extracting a brightness-minimum point (step S604) for each row. In the case of the example shown in FIG. 14A, the selected row has an X coordinate which is Xb.

Figure 14B:
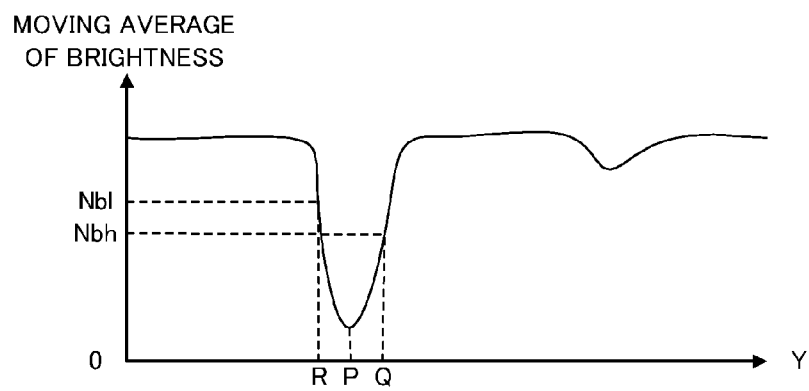
FIG. 14B is a diagram for explaining a (third) method of extracting a brightness minimal point.

Next, the CPU 34 obtains a moving average of respective brightness of the pixels configuring the selected row (step S602). For example, the CPU 34 calculates a moving average of brightness of 10 pixels successive in the Y-axis direction in an order of a smaller Y coordinate. FIG. 14B shows a relationship between the moving average of brightness and a Y coordinate in the row having an X coordinate which is Xb.

Figure 14C:
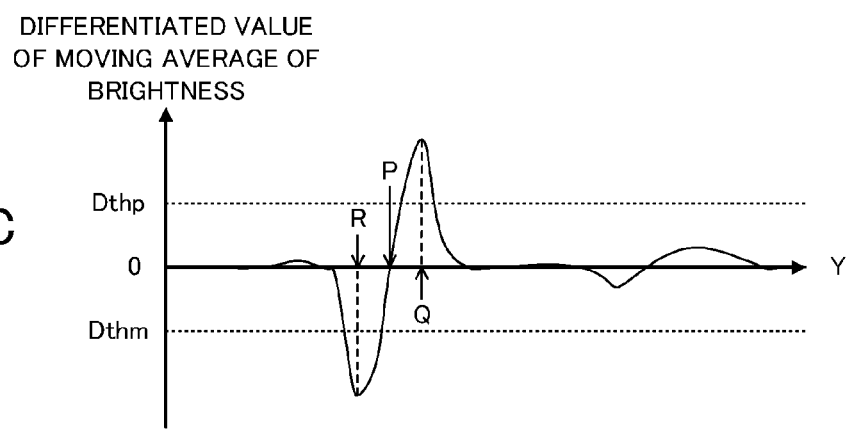
FIG. 14C is a diagram for explaining a (fourth) method of extracting a brightness minimal point.

Next, the CPU 34 differentiates the moving average of brightness obtained in the step S602 with a variable indicating a position in the Y-axis direction (step S603). FIG. 14C shows a relationship between a differentiated value of the moving average of brightness and a Y coordinate in the row having an X coordinate which is Xb.

Next, the CPU 34 extracts a brightness-minimum point (step S604). In the case of the example shown in FIG. 14C, first, the CPU 34 extracts a point P where a differentiated value changes from negative to positive. Next, for the detected brightness-minimum point P, the CPU 34 determines whether or not the brightness largely changes on some level. More specifically, regarding the brightness-minimum point P, the CPU 34 extracts a point R right before the differentiated value becomes minimum and a point Q right after the differentiated value becomes maximum, determines whether or not the point R is equal to or smaller than a predetermined threshold Dthm and determines whether or not the point Q is equal to or larger than a predetermined threshold Dthp.

In the case of the example shown in FIG. 14C, the point R is equal to or smaller than the predetermined threshold Dthm, and the point Q is equal to or larger than the predetermined threshold Dthp. Hence, the CPU 34 determines that the brightness-minimum point P is a point where the brightness largely changes on some level, and stores a moving average Nbl of the point R and a moving average Nbh of the point Q in the RAM 35.

Next, the CPU 34 determines whether or not extraction of a brightness-minimum point for all rows completes, i.e., whether or not the process from the step of detecting a brightness (step S601) to the step of extracting a brightness-minimum point (step S604) completes for all rows (step S605). When determining that extraction of a brightness-minimum point completes for all rows (step S605: YES), the CPU 34 sets a threshold of binarization (step S606). When determining that extraction of a brightness-minimum point does not complete yet for all rows (step S605: NO), the CPU 34 executes the process from the step of detecting a brightness (step S601) to the step of extracting a brightness-minimum point (step S604) for the row where extraction of a brightness-minimum point does not complete yet.

When determining that extraction of a brightness-minimum point completes for all rows (step S605: YES), the CPU 34 sets a threshold of binarization (step S606). The CPU 34 sets the threshold of the binarization based on the moving average Nbl of the point R and the moving average Nbh of the point Q extracted for each row. How to set the threshold of the binarization is optional, but following setting techniques (a) to (g) can be adopted.

(a) The threshold of the binarization is set based on the minimum value of the moving average Nbl of the point R of each row. (b) The threshold of the binarization is set based on the maximum value of the moving average Nbl of the point R of each row. (c) The threshold of the binarization is set based on the minimum value of the moving average Nbh of the point Q of each row. (d) The threshold of the binarization is set based on the maximum value of the moving average Nbh of the point Q of each row. (e) The threshold of the binarization is set based on the average value of the moving average Nbl of the point R of each row. (f) The threshold of the binarization is set based on the average value of the moving average Nbh of the point Q of each row. (g) The threshold of the binarization is set based on the average value of the moving average Nbl of the point R of each row and the moving average Nbh of the point Q of each row.

Next, the CPU 34 binarizes the image of the eye-vicinity range based on the threshold obtained in the binarization threshold setting (step S606) (step S607). The CPU, 34 obtains a binarized image (an image including black regions and white regions) of the eye-vicinity range through binarization. Upon generation of the binarized image, the CPU 34 completes the binarization process (step S403).

Next, the CPU 34 performs labeling on the binarized image (step S404). The CPU 34 performs labeling on black regions with respect to the binarized image generated by the binarization process (step S403), and obtains equal to or larger than one black regions (hereinafter, referred to as "labeled data").

When determining that there are plural pieces of labeled data, the CPU 34 selects a piece of labeled data (step S405). When, for example, the driver wears an eyeglass, pieces of labeled data like ones corresponding to the eyeglass in addition to labeled data corresponding to the eye through labeling may be detected. In this case, it is necessary for the CPU 34 to select a piece of labeled data corresponding to the eye among the plural pieces of labeled data.

How to select a labeled data corresponding to an eye is optional, but for example, the CPU 34 selects a labeled data having the maximum area among the pieces of labeled data which do not contact the upper end and the lower end of the eye-vicinity range as the labeled data corresponding to an eye.

Next, the CPU 34 detects the maximum continuous number of the pieces of labeled data (step S406). For the labeled data selected in the step of selecting labeled data (step S405), the CPU 34 obtains the maximum continuous number that black pixels continue longest in the Y-axis direction. The CPU 34 stores the obtained maximum continuous number as an eye open level in the RAM 35 in association with facial-expression estimation data. When completing detection of the maximum continuous number of pieces of labeled data, the CPU 34 completes the eye-open-level detection process (step S104).

Next, the CPU 34 determines whether or not the facial expression of the driver is a smile (step S105). More specifically, the CPU 34 determines whether or not the facial expression of the driver is a smile based on the estimated facial-expression data stored in the RAM 35 in the step of specifying the facial expression (step S303).

When determining that the facial expression of the driver is a smile (step S105: YES), the CPU 34 sets a threshold for a smiling facial expression (step S106).

The CPU 34 may read a threshold for each facial expression stored in the RAM 35 beforehand, or may obtain a threshold based on the record of the eye open level stored in the RAM 35 beforehand.

When the driver has a smiling facial expression, it can be estimated that the awakening level of the driver is high. Accordingly, a threshold with a small value is set for the smiling facial expression. For example, the CPU 34 obtains the average value of the eye open levels detected when the driver had a smiling facial expression among the record of the eye open level stored in the RAM 35, and a value ¼ of the average value is set as the threshold of the smiling facial expression.

Conversely, when determining that the facial expression of the driver is not a smile (step S105: NO), the CPU 34 determines whether or not the facial expression of the driver expresses squinting in the glare (step S107).

When determining that the facial expression of the driver expresses squinting in the glare (step S107: YES), the CPU 34 sets a threshold for squinting facial expression in the glare (step S108).

When the driver has a squinting facial expression in the glare, it can be estimated that the awakening level of the driver is high on some level. Accordingly, a threshold with a small value on some extent is set for the squinting facial expression in the glare. For example, the CPU 34 obtains an average value of the eye open levels detected when the driver had a squinting facial expression in the glare among the record of the eye open level stored in the RAM 35, and a value ½ of the average value is set as the threshold for the squinting facial expression in the glare.

When determining that the facial expression of the driver does not express squinting in the glare (step S107: NO), the CPU 34 determines whether or not the facial expression of the driver expresses sleepiness (step S109).

When determining that the facial expression of the driver expresses sleepiness (step S109: YES), the CPU 34 sets a threshold for the sleepy facial expression (step S110).

When the driver has a facial expression expressing sleepiness, it can be estimated that the awakening level of the driver is low. Accordingly, a threshold with a large value is set for the sleepy facial expression. For example, the CPU 34 obtains an average value of the eye open levels detected when it is determined that the eye is closed among the eye open levels stored in the RAM 35, a middle value between the average value and the maximum value of the eye open level stored in the RAM 35, and a middle value between the former middle value and the maximum value of the eye open level stored in the RAM 35 is set as the threshold for the sleepy facial expression.

Conversely, when determining that the facial expression of the driver is not a sleepy facial expression (step S109: NO), the CPU 34 sets a threshold of an eye open level for a normal facial expression (step S111).

For example, the CPU 34 obtains an average value of the eye open levels when it is determined that the eye is closed among the eye open levels stored in the RAM 35, and a middle value between the average value and the maximum value of the eye open level stored in the RAM 35 is set as the threshold for the normal facial expression.

When setting of the threshold for each facial expression completes (step S106, step S108, step S110, and step S111), the CPU 34 determines whether or not the eye open level is equal to or larger than the set threshold (step S112).

When determining that the eye open level is equal to or larger than the threshold (step S112: YES), the CPU 34 determines that the driver maintains an eye-opened condition, and stores data indicating that the driver maintains the eye-opened condition in the RAM 35 in association with the eye open level (step S113). Conversely, when determining that the eye open level is not equal to or larger than the threshold (step S112: NO), the CPU 34 determines that the driver is closing the eye, and stores data indicating that the driver is closing the eye in the RAM 35 in association with the eye open level (step S114). When completing determination of the opened/closed eye condition of the driver (step S113 and step S114), the CPU 34 completes the opened/closed eye determination process.

As explained above, the eye open/close recognizing apparatus 100 according to the first embodiment of the present invention determines the opened/closed eye condition of the driver based on the facial expression of the driver. More specifically, the eye open/close recognizing apparatus 100 estimates the facial expression of the driver, and changes a threshold for determination of the opened/closed eye condition based on the estimated facial expression of the driver. That is, when the estimated facial expression of the driver is a facial expression that the awakening level is possibly high, the threshold is set to be small, and when it is a facial expression that the awakening level is possibly low, the threshold is set to be high. In this fashion, the eye open/close recognizing apparatus 100 determines the opened/closed eye condition corresponding to a change in the eye condition that changes in accordance with the facial expression of the driver. Accordingly, it can be expected that the possibility of false determination for the opened/closed eye condition of the driver is reduced.

Second Embodiment

The eye open/close recognizing apparatus 100 of the first embodiment detects an eye open level and sets the threshold of the eye open level with any kind of facial expression of the driver, and determines whether or not the detected eye open level is equal to or larger than the threshold. However, when the driver has a facial expression which enables an estimation that the awakening level is high (or low), it is fine if the eye opened determination (or the eye closed determination) is performed without the eye open level being detected.

An explanation will now be given of an opened/closed eye condition determination process executed by the eye open/close recognizing apparatus 100 according to a second embodiment with reference to the flowchart of FIG. 15. The eye open/close recognizing apparatus 100 of the second embodiment employs the same configuration as that of the eye open/close recognizing apparatus 100 of the first embodiment, so that the duplicated explanation for the configuration will be omitted.

Figure 15:
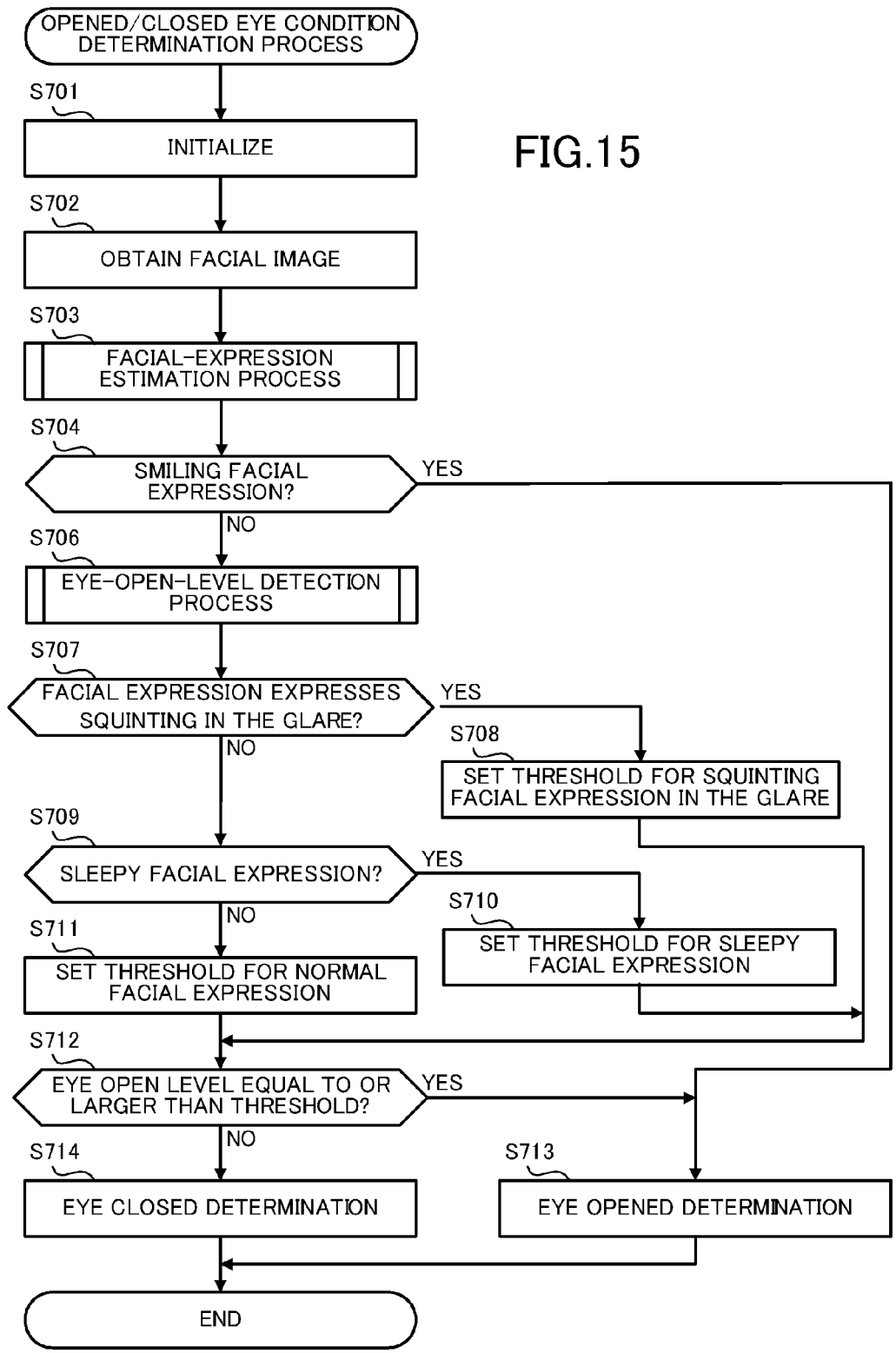
FIG. 15 is a flowchart showing an illustrative opened/closed eye condition determination process executed by the eye open/close recognizing apparatus according to the second embodiment of the present invention.

Upon power on of the eye open/close recognizing apparatus 100, the CPU 34 in the computer 30 periodically (e.g., ⅓₀ seconds) executes an opened/closed eye condition determination process shown in FIG. 15.

First, the CPU 34 executes, for example, initialization of a variable used in the opened/closed eye condition determination process (step S701).

Next, the CPU 34 obtains a facial image of a driver (step S702). More specifically, the CPU 34 supplies a facial image expressed by analog image signals by what corresponds to a frame output by the camera 10 to the A/D converter 31, and stores, in the image memory 32, a facial image expressed by digital image signals by what corresponds to a frame output by the A/D converter 31.

Next, the CPU 34 executes a facial-expression estimation process (step S703). That is, the eye open/close recognizing apparatus 100 executes the same process as the facial-expression estimation process shown in the flowchart of FIG. 8, thereby estimating the facial expression of the driver.

When completing the facial-expression estimation process (step S703), the CPU 34 determines whether or not the facial expression of the driver is a smile (step S704). More specifically, the CPU 34 determines whether or not the facial expression of the driver is a smile based on the estimated facial-expression data stored in the RAM 35 in the step of specifying a facial expression (step S303).

When the facial expression of the drive is a smile, it can be estimated that the awakening level of the driver is high. Accordingly, when determining that the facial expression of the driver is a smile (step S704: YES), the CPU 34 directly determines that the eye is opened, and stores data indicating that the driver maintains an eye-opened condition in the RAM 35 in association with the eye open level (step S713).

Conversely, when determining that the facial expression of the driver is not a smile (step S704: NO), the CPU 34 executes an eye-open-level detection process (step S706). The eye-open-level detection process executed by the CPU 34 in the step S706 is same as the eye-open-level detection process shown in the flowchart of FIG. 9, so that the duplicated explanation will be omitted.

When completing the eye-open-level detection process (step S706), the CPU 34 determines whether or not the facial expression of the driver expresses squinting in the glare (step S707).

When determining that the facial expression of the driver expresses squinting in the glare (step S707: YES), the CPU 34 sets a threshold of an eye open level for squinting facial expression in the glare (step S708).

When the facial expression of the driver expresses squinting in the glare, it can be expected that the awakening level of the driver is high on some level. Accordingly, a threshold with a small value on some extent is set for the squinting facial expression in the glare. For example, the CPU 34 obtains an average value of the eye open levels detected when the driver had a squinting facial expression in the glare among the record of the eye open level stored in the RAM 35, and a value ½ of the average is set as the threshold for the squinting facial expression in the glare.

Moreover, when determining that the facial expression of the driver does not express squinting in the glare (step S707: NO), the CPU 34 determines whether or not the facial expression of the driver expresses sleepiness (step S709).

When determining that the facial expression of the driver expresses sleepiness (step S709: YES), the CPU 34 sets a threshold of an eye open level for the sleepy facial expression (step S710).

When the driver has a facial expression expressing sleepiness, it can be expected that the awakening level of the driver is low. Accordingly, a threshold with a large value is set for the sleepy facial expression. For example, the CPU 34 obtains an average value of the eye open levels detected when it is determined that the eye is closed among the eye open levels stored in the RAM 35, a middle value between the average value and the maximum value of the eye open level stored in the RAM 35, and a middle value between the former middle value and the maximum value of the eye open level stored in the RAM 35 is set as the threshold for the sleepy facial expression.

Conversely, when determining that the facial expression of the driver is not a sleepy facial expression (step S709: NO), the CPU 34 sets a threshold of an eye open level for a normal facial expression (step S711).

For example, the CPU 34 obtains an average value of the eye open levels when it is determined that the eye is closed among the eye open levels stored in the RAM 35, and a middle value between the average value and the maximum value of the eye open level stored in the RAM 35 is set as the threshold for the normal facial expression.

When setting of the threshold for each facial expression completes (step S708, step S710, and step S711), the CPU 34 determines whether or not the eye open level is equal to or larger than the set threshold (step S712).

When determining that the eye open level is equal to or larger than the threshold (step S712: YES), the CPU 34 determines that the driver maintains an eye-opened condition, and stores data indicating that the driver maintains the eye-opened condition in the RAM 35 in association with the eye open level (step S713). Conversely, when determining that the eye open level is not equal to or larger than the threshold (step S712: NO), the CPU 34 determines that the driver is closing the eye, and stores data indicating that the driver is closing the eye in the RAM 35 in association with the eye open level (step S714). When completing determination of the opened/closed eye condition of the driver (step S713 and step S714), the CPU 34 completes the opened/closed eye determination process.

As explained above, the eye open/close recognizing apparatus 100 according to the second embodiment of the present invention performs eye opened determination without detecting an eye open level when estimating that the driver has a facial expression that the awakening level is possibly high. Accordingly, the process time for the opened/closed eye determination process can be shortened. According to the present embodiment, when the facial expression of the driver is a smile, it is estimated that the awakening level of the driver is high. However, the facial expression which enables to estimate that the awakening level is high is not limited to the smiling facial expression, and for example, it can be estimated that the awakening level of the driver is high when the facial expression is a squinting facial expression in the glare. Moreover, the eye closed determination can be performed without an eye open level being detected when it is estimated that the awakening level of the driver is low.

Third Embodiment

The eye open/close recognizing apparatus 100 of the first and second embodiments estimates a facial expression through a Kohonen neural network. However, how to estimate the facial expression of a driver is not limited to a technique through the Kohonen neural network, and can be a technique through, for example, a feed-forward neural network.

Figure 16:
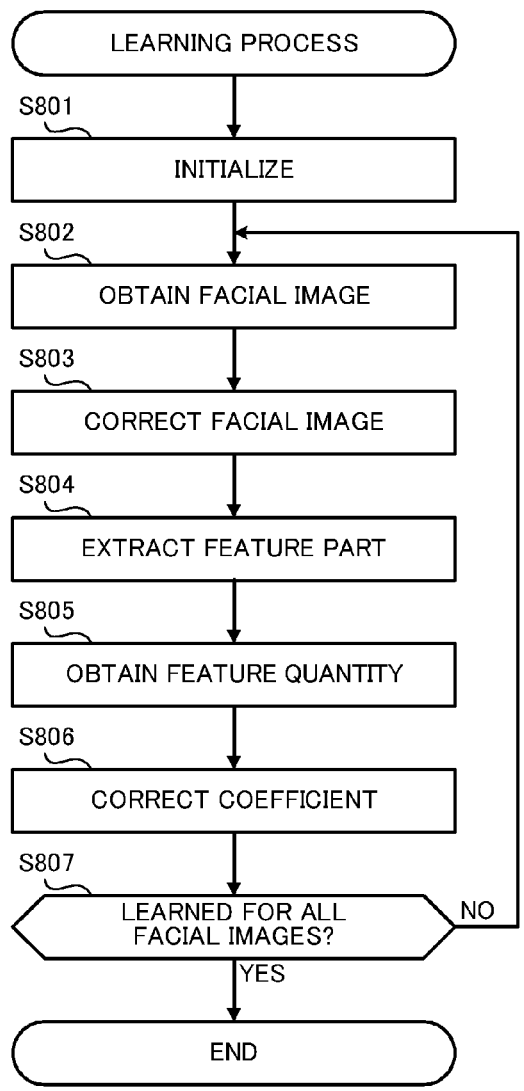
FIG. 16 is a flowchart showing an illustrative learning process executed by the eye open/close recognizing apparatus according to the third embodiment of the present invention.

First, an explanation will be given of a learning method through a feed-forward neural network with reference to the flowchart of FIG. 16.

The CPU 34 initializes, for example, a variable used for a learning process (step S801). Moreover, the CPU 34 gives a small value to each coefficient to be discussed later at random to initialize such a coefficient.

Next, the CPU 34 obtains a facial image for learning (step S802). For example, the CPU 34 supplies a facial image expressed by analog image signals by what corresponds to a frame output by the camera 10 to the A/D converter 31, and obtains, as a facial image for learning, a facial image expressed by digital image signals by what corresponds to a frame output by the A/D converter 31. Moreover, the CPU 34 obtains actual facial-expression data representing What facial expression the obtained facial image has. The CPU 34 obtains the actual facial-expression data from the user through, for example, the operation device 39.

The CPU 34 corrects the obtained facial image for learning into a facial image in a predetermined format (step S803). For example, the CPU 34 performs gray scaling on the obtained facial image for learning, and corrects the direction of the face and the size thereof based on the positions of both eyes through affine transformation, and stores the corrected facial image in the image memory 32.

Next, the CPU 34 extracts a feature part from the corrected facial image (step S804). The CPU 34 extracts a feature part that largely changes depending on the facial expression of the driver, such as an eye, an eyebrow, or a mouth, from the corrected facial image, and stores the image of the extracted feature part in the image memory 32.

Thereafter, the CPU 34 obtains a feature quantity of the feature part based on the image of the extracted feature part (step S805). For example, the CPU 34 extracts, as the feature quantity, the open level of the eye, the angle of the eyebrow, the open level of the mouth, etc.

The CPU 34 corrects the coefficient of each calculation in the feed-forward neural network (step S806). In the present embodiment, a multilayer perception is used as the feed-forward neutral network. An explanation will be briefly given of the feed-forward neural network with reference to FIG. 17.

Figure 17:
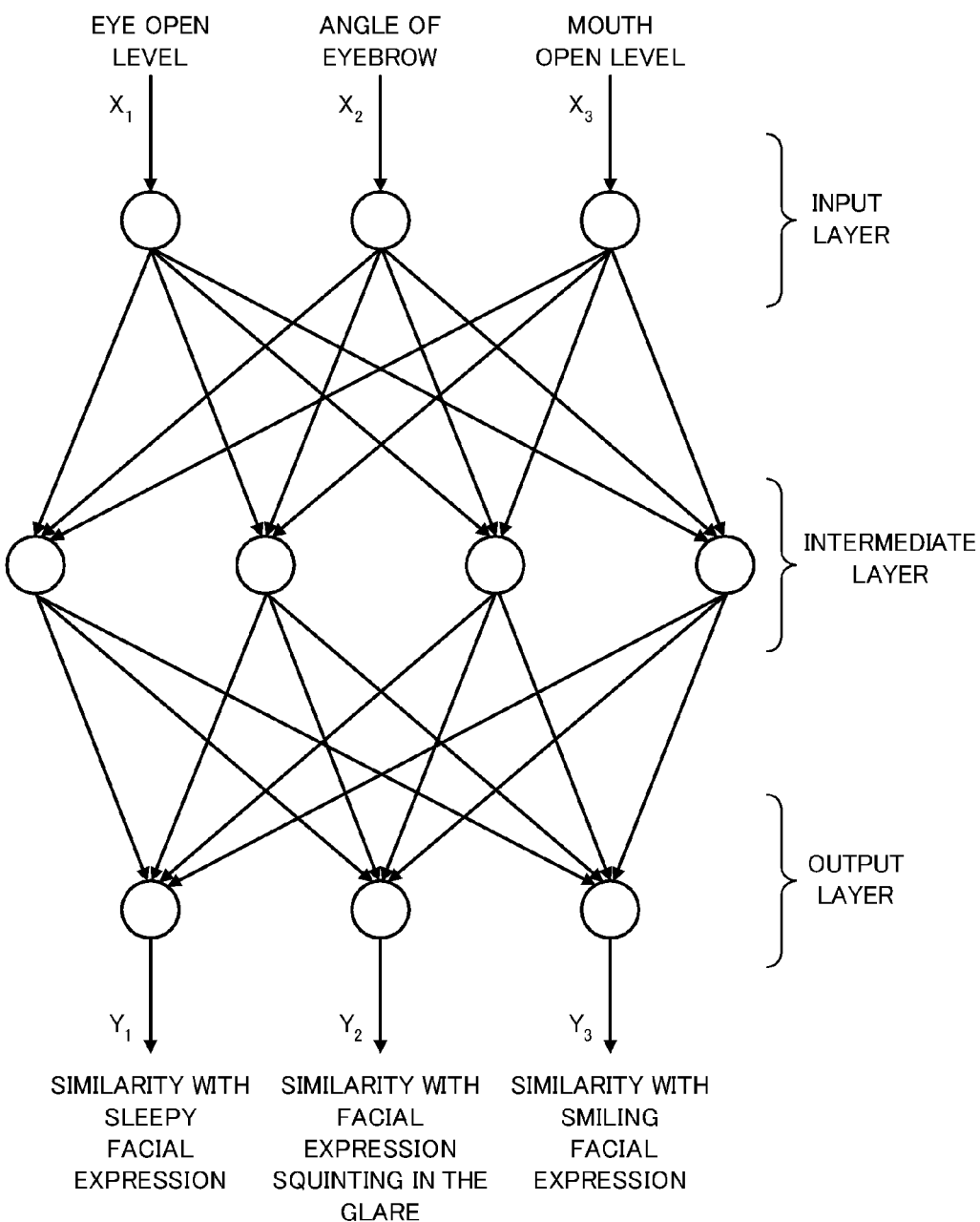
FIG. 17 is an exemplary diagram showing an illustrative feed-forward neutral network.
Figure 18:
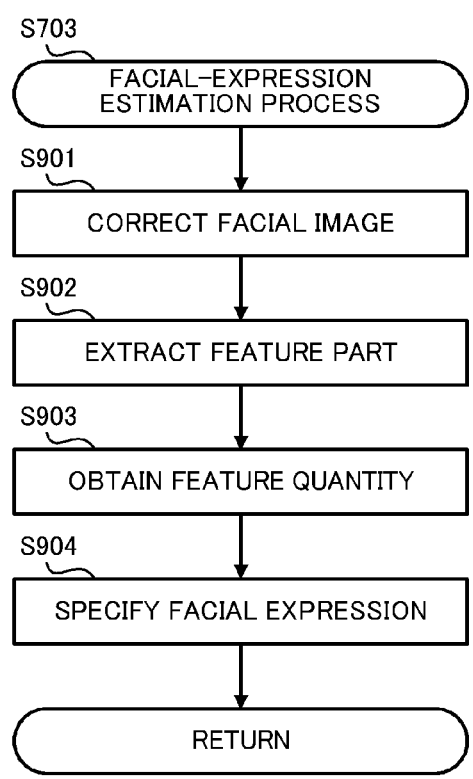
FIG. 18 is a flowchart showing an illustrative facial-expression estimation process executed by the eye open/close recognizing apparatus according to the third embodiment of the present invention.

As shown in FIG. 17, a feed-forward neural network includes three layers: an input layer; an intermediate layer; and an output layer. In the case of the example shown in FIG. 17, the input layer has three nodes, the intermediate layer has four nodes, and the output layer has three nodes.

When feature quantities are supplied to a node configuring the input layer as explanatory variables (independent variables), target variables (dependent variables) are calculated based on the explanatory variables, and the target variables are output through a node configuring the output layer. An explanation will now be given of how target variables are calculated from the explanatory variables.

When the explanatory variables are an open level $X_1$ of the eye, an angle $X_2$ of the eyebrow, and an open level $X_3$ of the mouth, and the target variables are a similarity $Y_1$ to a sleepy facial expression, a similarity $Y_2$ to a squinting facial expression in the glare, and a similarity $Y_3$ to a smiling facial expression, the feed-forward neural network is configured so that relationships expressed by following formulae (6) to (8) are satisfied. Note that $a_{11}$, $a_{12}$, $a_{13}$, $a_{21}$, $a_{22}$, $a_{23}$, $a_{31}$, $a_{32}$ and $a_{33}$ are each a coefficient weighting each explanatory variable.

[Equation 6]

$$Y_1 = a_{11}X_1 + a_{12}X_2 + a_{13}X_3 \quad (6)$$

[Equation 7]

$$Y_2 = a_{21}X_1 + a_{22}X_2 + a_{23}X_3 \quad (7)$$

[Equation 8]

$$Y_3 = a_{31}X_1 + a_{32}X_2 + a_{33}X_3 \quad (8)$$

The CPU 34 corrects each coefficient based on the explanatory variables, the target variables, and the actual facial-expression data obtained from the user in the step S802. More specifically, the CPU 34 corrects each coefficient so that the value of the target variable indicating the similarity to the facial expression represented by the actual facial-expression data among the three target variables becomes large. For example, when the facial expression represented by the actual facial-expression data is a smiling facial expression, each coefficient is corrected so that the similarity $Y_3$ to the smiling facial expression becomes large.

Next, the CPU 34 determines whether or not learning is performed by what corresponds to all facial images (step S807). The CPU 34 determines whether or not the current number of learning matches the total number of learning, and when determining that the current number of learning matches the total number of learning (step S807: YES), stores each coefficient in the setting memory 38 as setting information and completes the learning process. Conversely, when determining that the current number of learning does not match the total number of learning (step S807: NO), the process returns to the step of obtaining a facial image (step S802). That is, the CPU 34 repeats the process from the step of obtaining a facial image (step S802) to the step of correcting a coefficient (step S806) in order to repeat correction of the coefficients until determining that the current number of learning matches the total number of learning.

The CPU 34 executes the above-explained learning process before executing the facial-expression estimation process (step S703).

Next, an explanation will be given of the facial-expression estimation process executed by the eye open/close recognizing apparatus 100 according to the third embodiment of the present invention.

The CPU 34 corrects the facial image stored in the image memory 32 into a facial image in a predetermined format (step S901). For example, the CPU 34 performs gray scaling on the facial image stored in the image memory 32, corrects the direction of the face and the size thereof based on the positions of both eyes through affine transformation, and stores the corrected facial image in the image memory 32.

Next, the CPU 34 extracts a feature part from the corrected facial image (step S902). The CPU 34 extracts a feature part that largely changes depending on the facial expression of the driver, such as an eye, an eyebrow, or a mouth, from the corrected facial image, and stores the image of the extracted feature part in the image memory 32.

The CPU 34 obtains a feature quantity of the feature part based on the image of the extracted feature part (step S903). The CPU 34 extracts, for example, the open level of the eye, the angle of the eyebrow, the open level of the mouth as the feature quantity.

The CPU 34 specifies a facial expression (step S904). The CPU 34 obtains a similarity to each facial expression based on the feature quantity extracted in the step S903, and specifies the facial expression having the highest similarity obtained as the facial expression of the driver. The CPU 34 stores information indicating the specified facial expression in the RAM 35 as estimated facial-expression data.

When completing the step of specifying the facial expression (step S904), the CPU 34 completes the facial-expression estimation process (step S703).

The eye open/close recognizing apparatus 100 of the third embodiment estimates the facial expression of the driver through the feed-forward neural network. In this case, it is also possible to estimate the awakening level of the driver from the estimated facial expression of the driver, and thus it is expected that the possibility of false determination for opened/closed eye condition of the driver can be reduced. In this way, how to estimate the facial expression of the driver is not limited to any particular scheme.

Modified Example

The eye open/close recognizing apparatus 100 of the first to third embodiments changes the threshold depending on what facial expression the estimated facial expression is. However, the awakening level of the driver may be obtained from the estimated facial expression and the threshold may be set in accordance with the awakening level. For example, the eye open/close recognizing apparatus 100 of the third embodiment may obtain the awakening level $b_1Y_1+b_2Y_2+b_3Y_3$ in order to satisfy condition such that $b_1<0$, and $0<b_2<b_3$, and may set the threshold in accordance with the awakening level.

According to the first to third embodiments, the eye open/close recognizing apparatus 100 estimates a facial expression through the neural network. However, how to estimate a facial expression is not limited to the scheme through the neural network as long as a facial expression can be estimated from a facial image.

How to obtain an eye open level is optional and is not limited to the scheme explained in the first embodiment.

The first to third embodiments explained an example case in which the CPU 34 obtains a facial image obtained by picking up an image of the driver from the camera 10, and processes the facial image. However, the CPU 34 may obtain a facial image from the image memory 32 storing the facial image obtained by picking up an image of the driver beforehand, and may process such a facial image. In this case, the eye open/close recognizing apparatus 100 needs no camera.

According to the first embodiment, when the facial expression of the driver is a facial expression which enables general estimation that the awakening level of the driver is possibly high in general (e.g., a smiling facial expression, a squinting facial expression in the glare), the threshold of the eye open level is set to be a small value, and when it is a facial expression that the awakening level of the driver is possibly low in general (e.g., a sleepy facial expression), the threshold of the eye open level is set to be a large value. However, whether or not to determine that the awakening level of the driver is high (or low) based on what facial expression the driver has can be set arbitrarily.

For example, when the driver has a facial expression expressing that the driver possibly watches carefully a specific object (e.g., gauges, such as a speed meter, a tachometer, and an oil gauge) or a person (a passenger sitting down the front passenger seat), it is possible to determine that the awakening level of the driver is high and the threshold of the eye open level can be set to be a small value. An explanation will now be given of an opened/closed eye condition determination process executed by the eye open/close recognizing apparatus 100 according to a modified example with reference to the flowchart of FIG. 19. The process from initialization (step S1001) to an eye-open-level detection process (step S1004) is the same process as the opened/closed eye condition determination process shown in FIG. 3, so that the duplicated explanation will be omitted.

When completing the eye-open-level detection process (step S1004), the CPU 34 determines whether or not the facial expression of the driver expresses that the driver carefully watches a gauge of the vehicle (step S1005). When determining that the facial expression of the driver expresses that the driver carefully watches the gauge of the vehicle (step S1005: YES), the CPU 34 sets a relatively small threshold as the threshold for a facial expression of carefully watching the gauge of the vehicle (step S1006). Conversely, when determining that the facial expression of the driver does not express that the driver carefully watches the gauge of the vehicle (step S1005: NO), the CPU 34 sets a threshold of an eye open level for a normal facial expression (step S1007). Hereinafter, like the opened/closed eye condition determination process shown in FIG. 3, the CPU 34 compares an eye open level detected in the step S1004 with a threshold set in the step S1006 or the step S1007 (step S1008), and executes eye opened determination (step S1009) or eye closed determination (step S1010).

Like the opened/closed eye condition determination process shown in FIG. 19, when it is determined that the facial expression of the driver expresses that the driver carefully watches a specific object, the threshold of the eye open level is set to be a value which is likely to be determined that the eye is opened, thereby enabling appropriate determination whether or not the driver keeps opening the eye. When it is determined that the facial expression of the driver has a high eye open level (a facial expression expressing that the driver carefully watches a specific object), like the second embodiment, eye opened determination can be made without the eye open level being detected. It is easy to determine whether or not the facial expression of the driver expresses that the driver carefully watches the gauge of the vehicle through the estimation of the facial expression by the neural network.

The eye open/close recognizing apparatus of the preset invention can be realized not by an exclusive system but by a general computer system. For example, a program for executing the above-explained operations is stored in a computer-readable recording medium, such as a flexible disk, a CD-ROM (Compact Disk Read-Only Memory), a DVD (Digital Versatile Disk), or an MO (Magneto Optical Disk), and is distributed, and installed in a computer system to which a facial image is imputable, and the eye open/close recognizing apparatus that executes the above-explained processes can be realized.

Moreover, such a program may be stored in a disk device or the like of a server device over the Internet, and superimposed on a carrier wave in order to cause a computer to download such a program.

In the foregoing embodiments, the CPU 34 functions as image obtaining unit, facial-expression estimating unit, eye-open-level obtaining unit, threshold setting unit, and eye open/close determining unit. The present invention is, however, not limited to this case, and each of the image obtaining unit, the facial-expression estimating unit, the eye-open-level obtaining unit, the threshold setting unit, and the eye open/close determining unit may be realized by each hardware resource.

Moreover, in the foregoing embodiments, the RAM 35 functions as a record-information memory unit. The present invention is, however, not limited to this configuration, and a memory device like a hard disk can be used as the record-information memory unit.

The present invention is based on Japanese Patent Application No. 2008-320889 filed on Dec. 17, 2008. The whole specification, claims, and drawings of Japanese Patent Application No. 2008-320889 are herein incorporated in this specification by reference.

INDUSTRIAL APPLICABILITY

The eye open/close recognizing apparatus and recording medium of the present invention are appropriate for determining the opened/closed eye condition of a person subjected to image pickup.

DESCRIPTION OF REFERENCE NUMERALS

10 Camera
20 Light source
30 Computer
31 A/D converter
32 Image memory

33 ROM
34 CPU
35 RAM
36 Display control device
37 Light-source control device
38 Setting memory
39 Operation device
40 Display device
100 Eye open/close recognizing apparatus

The invention claimed is:

1. An eye open/close recognizing apparatus comprising:
    image obtaining unit that obtains an image of a face of a person subjected to image pickup;
    facial-expression estimating unit that estimates a facial expression of the person subjected to image pickup based on the image;
    eye-open-level obtaining unit that obtains an eye open level of the person subjected to image pickup based on the image;
    threshold setting unit that sets a threshold to be low when it is determined that facial expression estimated by the facial-expression estimating unit indicates that an awakening level is high, and sets the threshold to be high when it is determined that the facial expression estimated by the facial-expression estimating unit indicates that the awakening level is low; and
    eye open/close determining unit which determines that an eye of the person subjected to image pickup is opened upon determination that the eye open level exceeds the threshold, and which determines that the eye of the person subjected to image pickup is closed upon determination that the eye open level does not exceed the threshold.

2. The eye open/close recognizing apparatus according to claim 1, wherein the eye open/close determining unit determines that the eye of the person subjected to image pickup is opened regardless of the eye open level when it is determined that the facial expression estimated by the facial-expression estimating unit indicates that the awakening level is high, and determines that the eye of the person subjected to image pickup is closed regardless of the eye open level when it is determined that the facial expression estimated by the facial-expression estimating unit indicates that the awakening level is low.

3. The eye open/close recognizing apparatus according to claim 1, wherein the threshold setting unit determines that a smiling facial expression, a squinting facial expression in the glare or a facial expression of watching an object in a specific direction is a facial expression indicating that the awakening level is high.

4. The eye open/close recognizing apparatus according to claim 1, wherein the threshold setting unit determines that a sleepy facial expression is a facial expression indicating that the awakening level is low.

5. The eye open/close recognizing apparatus according to claim 1, wherein the threshold setting unit determines that a facial expression of watching a gauge of a vehicle driven by the person subjected to image pickup is a facial expression indicating that the awakening level is high.

6. The eye open/close recognizing apparatus according to claim 1, further comprising record information memory unit that stores, as record information, information indicating the facial expression estimated by the facial-expression estimating unit in association with information indicating the eye open level,
    wherein the threshold setting unit sets the threshold based on the record information.

7. The eye open/close recognizing apparatus according to claim 6, wherein the record information memory unit further stores, as the record information, the information indicating a facial expression estimated by the facial-expression estimating unit and the information indicating the eye open level in association with information indicating a determination result by the eye open/close determining unit.

8. The eye open/close recognizing apparatus according to claim 1, wherein the facial-expression estimating unit estimates a facial expression of the person subjected to image pickup based on the image using a neural network.

9. The eye open/close recognizing apparatus according to claim 8, wherein the neural network is a Kohonen type neural network.

10. The eye open/close recognizing apparatus according to claim 1, wherein the eye-open-level obtaining unit extracts an image including the eye of the person subjected to image pickup from the image, performs binarization on the extracted image, and obtains, as the eye open level, the maximum value of the number of pixels which are arranged consecutively in the vertical direction of the eye of the person subjected to image pickup and which have predetermined brightness.

* * * * *